United States Patent [19]

Gandolfi et al.

[11] 4,041,064

[45] Aug. 9, 1977

[54] 16-METHYL PROST-5-EN-13-YNOIC ACID DERIVATIVES

[75] Inventors: Carmelo Gandolfi; Gianfederico Doria; Renato Pellegata; Maria M. Usardi, all of Milan, Italy

[73] Assignee: Carlo-Erba S.p.A., Milan, Italy

[21] Appl. No.: 600,187

[22] Filed: July 29, 1975

[30] Foreign Application Priority Data

Sept. 17, 1974 Italy ................................. 27333/74

[51] Int. Cl.$^2$ .......................................... C07C 177/00

[52] U.S. Cl. ............................ 560/121; 260/343.3 R; 260/514 D; 260/346.22; 542/426; 424/305; 424/317

[58] Field of Search ................ 260/468 D, 514 D, 69

[56] References Cited

U.S. PATENT DOCUMENTS 3,935,254   1/1976   Gandolfi et al. ..................... 260/514

*Primary Examiner*—Robert Gerstl
*Attorney, Agent, or Firm*—Cushman, Darby & Cushman

[57] ABSTRACT 16S and 16R methyl 13, 14 dehydro PGE$_2$ compounds have been prepared.

13 Claims, No Drawings

16-METHYL PROST-5-EN-13-YNOIC ACID DERIVATIVES

German "Offenlegungsschrift" No. P 23 18785.1 describes a general method for the preparation of new 9,11,15-trihydroxy-13,14-dehydro-prostaglandins (9α-hydroxy derivatives of the natural series and 9β-hydroxy derivatives of the enantio series) by the reaction of a chloro-lactol derivative of formula

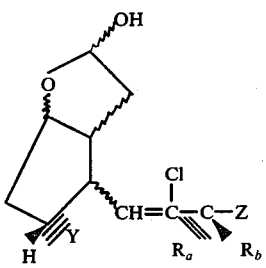

wherein one of $R_a$ and $R_b$ is hydrogen and the other is hydroxy or a known protecting group bound to the chain through an ethereal oxygen atom, and Y is hydroxy or a known protecting group bound to the ring through an ethereal oxygen atom, with a Witting reagent containing the desired substituents.

This reaction however presents several inconveniences in that, to avoid formation of 14-chloro- $\Delta^{13(14)}$-ethyl prostaglandin analogues, it is necessary, by using for example 1.5 to 2.5 moles of Wittig reagent per mole of lactol, to prolong the reaction time up to ten hours or, if it is desired to use shorter reaction times, it is necessary to employ a great excess of Wittig reagent (at least 5 moles of Wittig reagent per mole of lactol for reaction times of about 30 minutes).

It has been now found that the replacement of the chlorine atom with a bromine or iodine atom, preferably with a bromine atom, in the lactol used as starting material, allows to obtain, with practically quantitative yields, exclusively 9,11,15-trihydroxy-13,14-dehydro-prostaglandin derivatives, independently from molar ratios of the reagents (a 1:2 molar ratio is sufficient) and also for very short reaction times (for example 10–20 minutes ) without the formation of 9, 11,15-trihydroxy-14-halo-13,14-ethylene derivatives.

It is therefore an object of the present invention a general method for the preparation of 9α,11α,15(S or R)-trihydroxy-13,14-dehydro-prostaglandins of the natural series and 9β,11α,15(S or R)-trihydroxy-13,14-dehydro-prostaglandins of the enantio-series, said method comprising the reaction of an optically active or racemic lactol of formula (A)

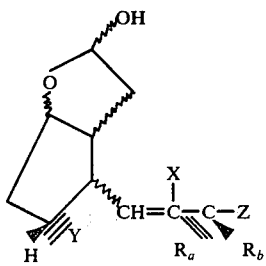

wherein

Y, $R_a$ and $R_b$ are as above defined, X is bromine or iodine, and Z is a generic residue of the side chain,
with a Witting reagent containing the desired substituents, the subsequent optional deetherification, saponification, re-esterification, and/or salification of the obtained compound.

In the lactol of the above formula, the two bonds of the lactol ring indicated by the wavy line attachment ( ) are in the cis-configuration, i.e. they are both below the plane of the cyclopentane ring or both above the plane of the cyclopentane ring, while the side-chain is in the transconfiguration with respect to the lactol ring, i.e. it is below the plane of the cyclopentane ring when the lactol ring is above the plane of the cyclopentane ring, and vice versa In the lactol of formula (A), as well as in the lactols of formulae (A') and (A"), the hydrogen atom linked to the carbon atom in the 13- position and the halogen atom linked to the carbon atom in the 14- position (prostaglandin numbering) are preferably in the trans-position (geometric trans-isomers), but they may be also in the cis-position (geometric cis-isomers). The lactol hydroxy group may be either in the α-configuration, i.e. below the plane of the lactol ring, or in the β-configuration, i.e. above the plane of the lactol ring. The starting material may therefore be either an optically active or racemic compound of formula (A')

(A')

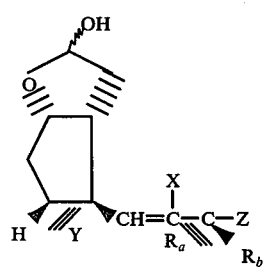

or an optically active or racemic compound of formula (A")

(A")

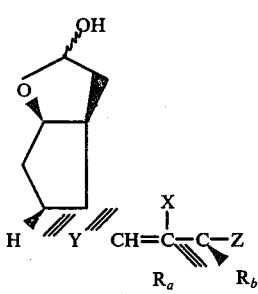

When the compound of formula (A') is used as a starting material, a 9α, 11α,15(S or R)-trihydroxy-13,14-dehydro-prostaglandin derivative is obtained, while, when the compound of formula (A") is used as starting material, a 9β,11α,15(S or R)-trihydroxy-13,14-dehydro-8,12-diiso prostaglandin derivative is obtained. As stated above, the reaction of the halo-lactol with the Wittig reagent is preferably performed using about two moles of Wittig reagent per mole of lactol.

The reaction is carried out by using the conditions generally followed for this reaction, i.e. in an organic solvent, for example diethyl ether, hexane, dimethyl sulphoxide, tetrahydrofuran, dimethylformamide or hexamethylphosphoramide, in presence of a base, preferably sodium hydride and potassium tert.-butoxide, at 0° C to the reflux temperature of the reaction mixture, preferably at room temperature or below.

As stated above, it is sufficient that the reaction lasts 10-20 minutes, depending on the temperature and concentration of the reaction mixture and the specific Witting reagent used.

The term "Wittig reagent" includes compounds of general formula

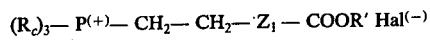

wherein $R_c$ is aryl or alkyl, Hal is bromine or chlorine, $Z_1$ is the substituent which is desired to be present in the side-chain linked to the carbon atom in the 8-position of the prostaglandin obtained by the reaction of the halo-lactol with the Wittig reagent, and — COOR' is a carboxy group or a generic carboxy ester. When $R_c$ is alkyl, it is preferably ethyl.

The preparation of the Wittig reagents is discussed in detail by Tripett, Quart. Rev., 1963, XVII, No. 4, 406.

When the side-chain of the halo-lactol contains one (or more) hydroxy group(s), said hydroxy group(s) may be protected, as well as the hydroxy group in the 11-position, in a conventional manner by means of known protecting groups bound to the chain through an ethereal oxygen atom.

The known protecting groups (i.e. either groups) should be convertible to hydroxy groups under mild reaction conditions, e.g. acid hydrolysis. Examples are acetalic ethers, enol ethers, and silyl ethers. The preferred groups are

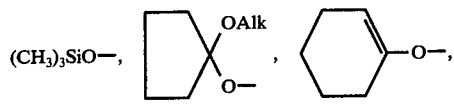

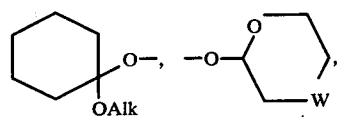

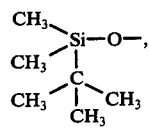

wherein W is —O— or —CH$_2$— and Alk is a lower alkyl group.

The optional deetherification of the compound obtained by the reaction of the halo-lactol with the Wittig reagent is performed under conditions of mild acid hydrolysis, for example with mono- or poly-carboxy acid e.g. formic, acetic, oxalic, citric and tartaric acid, and in a solvent, for example water, acetone, tetrahydrofuran, dimethoxyethane and lower aliphatic alcohols. Preferably, 0.1N to 0.25N polycarboxylic acid (e.g. oxalic or citric acid) is used in presence of a convenient low boiling co-solvent which is miscible with water and which can be easily removed in vacuo at the end of the reaction.

The optional saponification, re-esterification and/or salification steps of the compound obtained by the reaction of the halo-lactol with the Wittig reagent may be performed in a conventional manner, following the usual methods of organic chemistry.

The reaction of the halo-lactol of formula (A) with the Wittig reagent to give a 9α,11α,15(S or R)-trihydroxy-13,14-dehydro-prostaglandin of the natural series or a 9β,11α,15(S or R)-trihydroxy-13,14-dehydro-prostaglandin of the enantio series takes place, with quantiative yields and with the above-reported advantages, independently from the values of Z and $Z_1$ hereabove mentioned.

It is evident that the 9,11,15-trihydroxy-13,14-dehydro-prostaglandins so obtained, may be useful starting materials for the preparation of other 13,14-dehydro-prostaglandins, for example 13,14-dehydro-PGE derivatives.

The halo-lactol (bromo-lactol or iodo-lactol)of formula (A) used as starting material, may be prepared starting from an optically active or racemic lactone of formula (C)

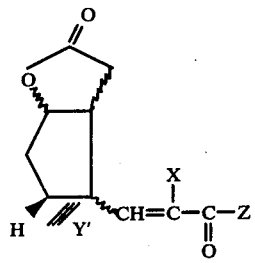

wherein

Y' is hydroxy, acyloxy or a known protecting group bound to the ring through an ethereal oxygen atom;

Z and X are as above defined;

and wherein the lactone ring is in the trans-configuration with respect to the side-chain, and wherein the hydrogen atom linked to the carbon atom in the 13- position and the halogen atom linked to the carbon atom in the 14- position (prostaglandin numbering) may be either in the trans-position or in the cis-position.

The halo-lactone may be therefore either an optically active or racemic compound of formula (C')

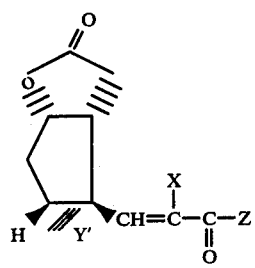

or an optically active or racemic compound of formula (C'')

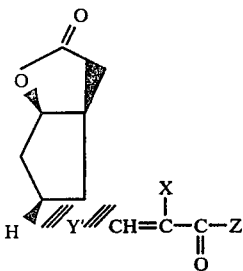

(C")

The multi-step process to obtain the halo-lactol of formula (A) involves the following steps:
1. reduction of the 15-oxo-group (prostaglandin numbering) of the lactone of formula (C) to yield a mixture of the 15S- and 15R-ols having the formulae (D) and (D')

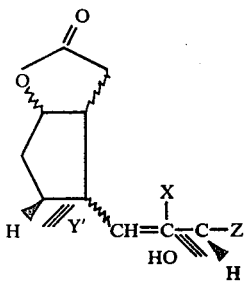

(D) (15S-ol)

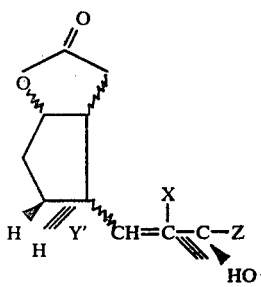

(D') (15R-ol)

wherein X, Y' and Z are as hereabove defined.

The reduction of the 15-oxo-group may be suitably performed in an organic solvent, such as acetone, diethyl ether, dimethoxy, ethane, dioxan or benzene and their mixtures, by using e.g. metal borohydrides, in particular sodium borohydride, lithium borohydride, zinc borohydride, sodium trimethoxyborohydride.

2. Separation of the 15S-ol frm the 15R-ol. This separation may be performed by chromatography e.g. silica gel chromatography or high presssure liquid chromatography, as well as by fractionated crystallisation.

3. Conversion of a compound of formula (E)

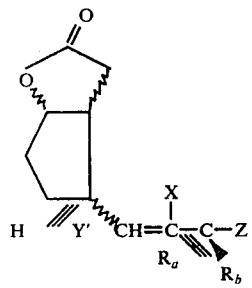

(E)

wherein X, Y' and Z are as hereabove defined, and one of $R_a$ and $R_b$ is hydrogen atom and the other is a hydroxy group into a compound of formula (F)

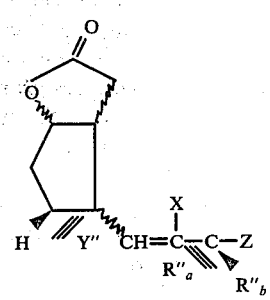

wherein X and Z are as above defined, Y" is a known protecting group bound to the ring through an ethereal oxygen atom and one of $R''_a$ and $R''_b$ is a known protecting group bound to the chain through an ethereal oxygen atom, and the other is a hydrogen atom.

The etherification of the compound of formula (E) to give a compound of formula (F) is preceded, when Y' in the compound of formula (E) is an aliphatic, aromatic, or cycloaliphatic carboxylic acyloxy group, by saponification, for example by mild treatment with an alkali, to give a compound of formula (E) wherein Y' is a hydroxy group.

The etherification is preferably carried out with a vinylic ether of formula

wherein W is —O— or —CH$_2$—, in presence of catalytic amounts of for example phosphorus oxychloride, p-toluenesulphonic acid or benzenesulphonic acid, or with a silyl ether, for instance by reacting a trisubstituted chlorosilane in presence of an acceptor base (for example a trialkylamine) of the hydrogen halide formed, or with an enol ether, for instance by reaction, in presence of an acid catalyst with a 1,1-dialkoxy-cyclopentane or cyclohexane, at the reflux temperature in an inert solvent and distilling the alcohol formed to obtain mixed dialkoxy ethers or enol ethers, according to the quantity of catalyst used or the heating time.

4. Reduction of the compound of formula (F) to yield a lactol derivative of formula (G)

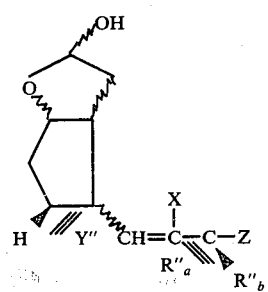

(G)

wherein X, Y", $R''_a$, $R''_b$ and Z are as hereabove defined. The reduction may be performed by treatment with diisobutylaluminium hydride or sodium bis-(2- methoxyethoxy) aluminium hydride in an inert solvent, for example toluene, n-heptane, n-hexane or benzene or their mixtures, at below −30° C.

5. Optional deetherification of the compound of formula (G) to give a compound having the free 11- and 15-hydroxy groups.

The deetherification may be carried out by mild acid hydrolysis, in a solvent miscible with water, with a solution of a mono- or poly-carboxylic acid.

In all the compounds mentioned under 1) to 5) above, which can be either optically active compounds or racemic mixtures thereof, the lactol ring or the lactone ring is in the trans-configuration with respect to the side-chain.

The lactone of formula (C) may be in turn prepared in an only one step by reaction of an aldehyde of formula (H)

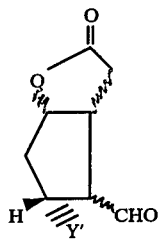

(H)

wherein Y' is as above defined, with a phosphonate of formula (L)

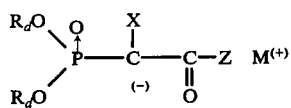

(L)

wherein X and Z are as hereabove defined, $R_d$ is lower alkyl and $M^{(+)}$ is a cation of a base, in particular sodium. The reaction is suitably performed in a solvent which is preferably dry benzene, dimethoxyethane, tetrahydrofuran, dimethylformamide or their mixtures, and using a suspension of 1.1–1.2 molar equivalents of the compound of formula (L) per each mole of aldehyde.

Starting material for this one-step process may therefore be an optically active or racemic aldehyde of formula (H')

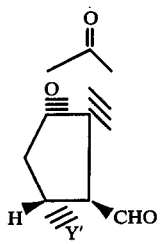

(H')

wherein Y' is as hereabove defined or an optically active or racemic aldehyde of formula (H'')

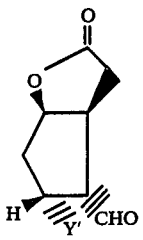

(H'')

wherein Y' is as hereabove defined.

The aldehyde of formula (H') may be prepared substantially as described by E. J. Corey et al., Annals of N.Y. Ac. of Sciences, 180, 24 (1971) while the aldehyde of formula (H'') may be prepared substantially as described by C. Gandolfi et al., Tetrahedron Letters No. 42, 4303–4306 (1972).

The phosphonate of formula (L) may be prepared by means of a halogenating agent selected from the group consisting of $Br_2$, pyrrolidonehydrotribromide (PHTB), N-bromo-succinimide, N-bromo-acetamide, N-bromo-caprolactame, dioxandibromide, N-iodo-succinimide, starting from the phosponate of formula (N)

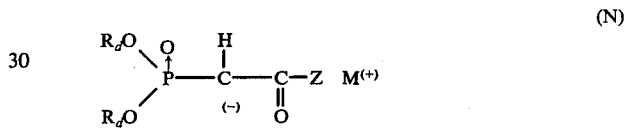

(N)

wherein $R_d$, Z and $M^{(+)}$ are as defined above, which may be prepared by reaction of a phosphonate of formula (P)

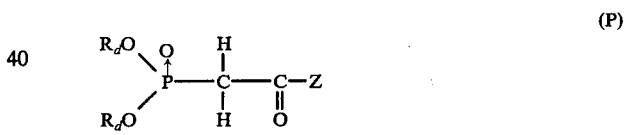

(P)

with an equivalent of a base, e.g. sodium, lithium or calcium hydride.

By using N-bromo- and N-iodo-imides as halogenating agents, the carbanion of the halo-phosphonate is obtained directly with the use of only one equivalent of base; otherwise, it should be necessary to use another equivalent of a base to obtain the carbanion of the halo-phosphonate.

The phosphonates of formula (P) may be prepared by known methods, e.g. according to E. J. Corey et al., J. Am. Chem. Soc., 90, 3247 (1968) and E. J. Corey and G. K. Kwiatkowsky, J. Am. Chem. Soc., 88, 5654 (1966). Preferably, the phosphonates of formula (P) may be prepared by reaction of lithium methylphosphonate with a lower alkyl ester of the suitable aliphatic acid. When the said aliphatic acid contains asymmetric carbon atoms, it will be possible to use either the racemic acid or one of its optical antipodes. Alternatively, the halo-lactone of formula (C) wherein X is bromine, may be prepared by a multi-step process starting from a trans-enone lactone of formula (Q),

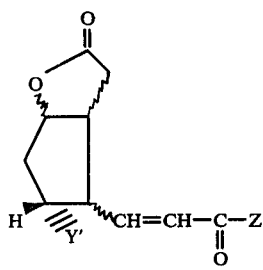

wherein Y' and Z are as defined above.

Starting material for this process may therefore be an optically active or racemic lactone of formula (Q')

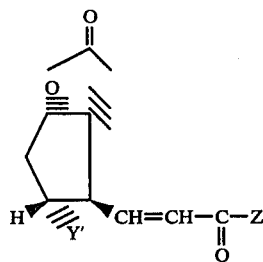

or an optically active or racemic lactone of formula (Q")

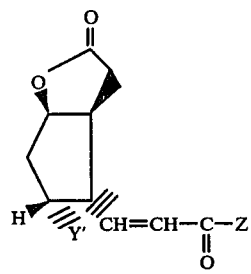

The lactone of formula (Q') may be prepared substantially as described by E. J. Corey et al., Annals of N.Y. Ac. of Sciences, 180, 24 (1971), while the lactone of formula (Q") may be prepared substantially as described by C. Gandolfi et al., Tetrahedron Letters, No. 42, 4303–4306 (1972).

This multi-step process involves the following steps:
1. reduction of the lactone of formula (Q) to give a mixture of the 15S- and 15R-ols of the formulae (R) and (R')

(R) (15S-ol)

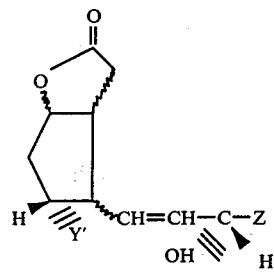

(R') (15R-ol)

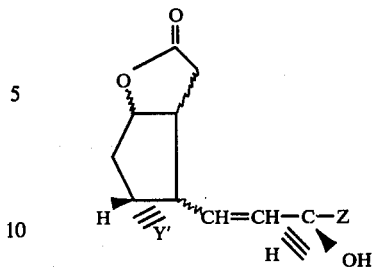

wherein Y' and Z are as hereabove defined.

The reduction may be performed in an organic solvent, such as acetone, diethyl ether and dimethoxyethane, by using for example, sodium borohydride, zinc borohydride, and lithium borohydride.

2. Halogenation of the mixture of the two 15R- and 15S- ols to give a mixture of 13ξ, 14ξ, dibromoalcohols of formulae (T) and (T')

(T) (15S-ol)

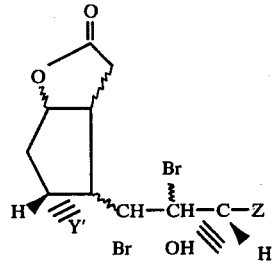

(T') (15R-ol)

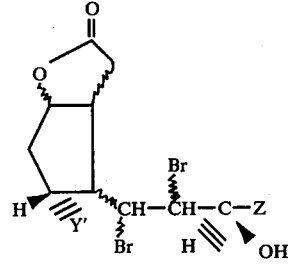

wherein Y' and Z are as hereabove defined.

The halogenation is carried out in an inert solvent, preferably selected from the group consisting of a halogenated solvent (dichloromethane, dichloroethane, CCl₄) and a linear or cyclic ether (tetrahydrofuran, dioxan, dimehoxyethane, or this mixtures), using the molar equivalent of halogenating agent or an excess of the same agent, which may be, e.g., Br₂, pyrrolidone hydrotribromide or dioxanbromide.

3. Oxidation of the mixture of the 13ξ, 14ξ, dibromoalcohols to give a 13,14-ξdibromo-15-oxo-derivative of formula (U)

(U)

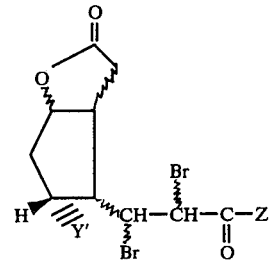

wherein Y' and Z are as above defined.

The oxidation is carried out at a temperture ranging between −25° C and the room temperature, by using a dichloromethane solution of the pyridine-chromic anhydride complex or a solphoric solution of chromic anhydride in acetone (Jones reagent), or a carbodiimide, working in dimethylsulphoxide in presence of a suitable acid.

4. Dehydrohalogenation of the 13,14- -dibromo-15-oxo-derivative, to give the compound of formula (C) wherein X is bromine.

The dehydrohalogenation may be performed by using an organic base, for example a tert.-amine in an inert solvent, or alternatively by using an inorganic base, for example potassium acetate in a solvent such as methanol, ethanol, and the like.

A further alternative process for the preparation of the halo-lactone of formula (C) wherein X is bromine is the reaction of a lactone of formula (Q), in an ethereal anhydrous solvent such as tetrahydrofuran and dimethoxyethane, with a halogenating agent such as phenyltrimethylammoniumtribromide (PTAT) and in particular pyrrolidonehydrotribromide (PHTB) (1,1–1,3 molar equivalents) to give directly the 13,14-dibromoderivative of formula (U) which is then dehydrohalogenated as above described, to give the compound of formula (C) wherein X is bromine.

Also in the alternative methods for the preparation of the lactone of formula (C), all the compounds may be either optically active compounds or racemic mixtures thereof and the lactone ring is in the trans-configuration with respect to the side-chain. In the preparation of the halo-lactone of formula (C) according to the here-above described methods, both compounds wherein the hydrogen atom linked to the carbon atom in the 13- position and the halogen atom linked to the carbon atom in the 14- position (prostaglandin-numbering) are in the trans-position (geometric trans-isomers) and compounds wherein said atoms are in the cis-position (geometric cis-isomers) are obtained, either the compounds belong to the natural or to the enantio series. The geometric trans-isomers are obtained in a far higher percentage (92–95%), while the geometric cis-isomers are obtained in a far lower percentage (5–8%). The geometric trans-isomers of formula

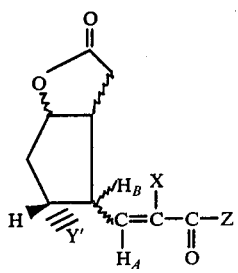

can be easily distinguished from the geometric cis-isomers of formula

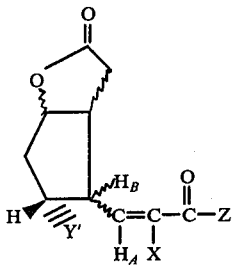

in that the $H_A$ vinylic protons of the two isomers resonate at different positions and the coupling constants of the $H_A$ vinylic proton with the $H_B$ proton are well different (respectively 9 Hz for the trans-isomer and 10.2 Hz for the cis-isomer).

Anyway, both the trans-isomers and the cis-isomers are intermediates for the synthesis of the 13,14-dehydroprostaglandins of the invention.

Another object of the present invention are new optically active or racemic compounds of the following general formula (I)

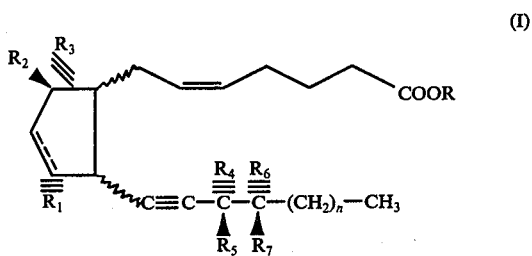

wherein R is a hydrogen atom, a $C_1$–$C_{12}$ alkyl group or a cation of a pharmaceutically acceptable base;

The symbol ----- represents a single or a double bond, wherein when the symbol --- is a double bond, $R_1$ is a hydrogen atom and $R_2$ and $R_3$ together form an oxo group, while when the symbol --- is a single bond, $R_1$ is hydroxy and one of $R_2$ and $R_3$ is hydrogen, and the other is hydroxy or $R_2$ and $R_3$ together form an oxo group; one of $R_4$ and $R_5$ is a hydrogen atom and the other is hydroxy; one of $R_6$ and $R_7$ is hydrogen, and the other is a 16(S) or 16(R) $C_1$–$C_4$ alkyl; n is an integer of 3 to 6; and wherein the chains bound to the carbon atoms in the 8- and 12- positions have a trans-configuration. The double bond in the 5(6)-position is a cis-double bond. In the formulae of this specification, the broken lines (⋯) indicate that the substituents are in the α-configuration, i.e. are below the plane of the ring or of the chain, while the heavy solid lines (—) indicate that the substituents are in the β-configuration, i.e. above the plane of the ring or of the chain; the wavy line attachment (∫) indicates that the groups may be either in the α-configuration, i.e. below the plane of the ring, or in the β-configuration, i.e. above the plane of the ring.

As stated above, the chains bound to the carbon atoms in the 8- and 12- position must have a trans-configuration, i.e. these chains cannot be both in the α-configuration or both in the β-configuration; when one of them is in the α-configuration, the other is in the β-configuration and vice versa.

As is evident from formula (I), the hydroxy group linked to the carbon atom in the 15- position may be either in the α-configuration

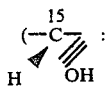

15S-ols) or in the β-configuration

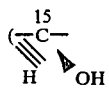

15R-ols).

Also the alkyl group linked to the carbon atom in the 16- position may be either in the α-configuration

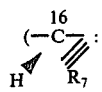

16S-alkyl compound) or in the β-configuration

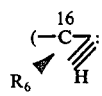

16R-alkyl compound); in other words, the alkyl group linked to the carbon atom in the 16- position can never be a 16(S,R) derivative, i.e. it can never be a mixture of the two 16R- and 16S- diastereoisomers.

It is also evident that when the symbol - - - - represents a double bond and therefore $R_1$ is a hydrogen atom, this hydrogen atom, being linked to a carbon atom which is no more asymmetric, may be obviously in an only one fixed position, i.e. on the plane of the ring, and therefore it may be neither in the α-position (i.e. below the plane of the ring) nor in the β-position (i.e. above the plane of the ring).

New compounds of the invention are therefore either optically active compounds having the general formulae

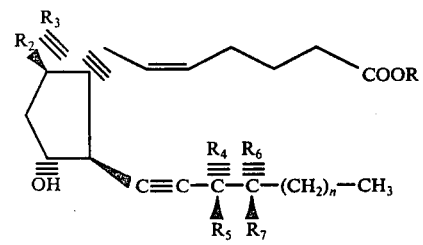

or optically active compounds having the general formulae

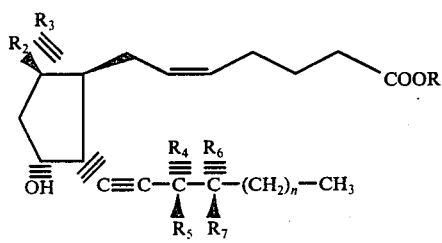

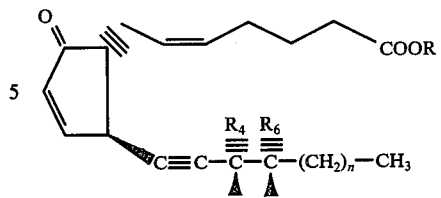

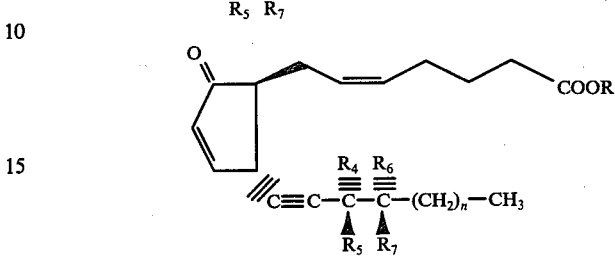

and their racemates.

When R is a $C_1$–$C_{12}$ alkyl group, it is preferably a methyl, either or heptyl group; n is preferably 3 or 4. The alkyl groups may be branched or straight chain.

Examples of cations of pharmaceutically acceptable bases are either metallic cations, such as sodium, potassium, calcium and aluminum, or organic amine cations, such as trialkylamines.

Examples of preferred compounds of the invention are the following 16S-methyl-5c-9-oxo-11α,15S-dihydroxy-prost-5-en-13-ynoic acid (or 16S-methyl-13,14-dehydro-PGE$_2$);

16R-methyl-5c-9-oxo-11α,15S-dihydroxy-prost-5-en-13-ynoic acid (or 16R-methyl-13,14-dehydro-PGE$_2$);

16S-methyl-5c-9-oxo-11α,15R-dihydroxy-prost-5-en-13-ynoic acid (or 16S-methyl-13,14-dehydro-15-epi-PGE$_2$);

16R-methyl-5c-9-oxo-11α,15R-dihydroxy-prost-5-en-13-ynoic acid (or 16R-methyl-13,14-dehydro-15-epi-PGE$_2$);

16S-methyl-5c-9-oxo-11α,15S-trihydroxy-8,12-diisoprost-5-en-13-ynoic acid (or 16S-methyl-13,14-dehydro-ent-11,15-epi-PGE$_2$).

The ω-homo compounds are those wherein n is 4, while the ω-dihomo compounds are those wherein n is 5.

The compounds of general formula (I) may be prepared by a process comprising reacting an optically active compound, or a racemic mixture of compounds, of general formul (II)

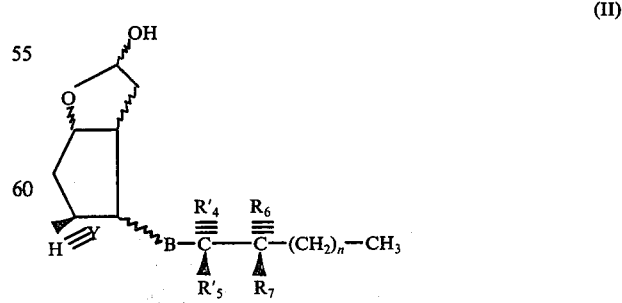

(II)

wherein B may be -C ≡ C- or -CH =

(III)

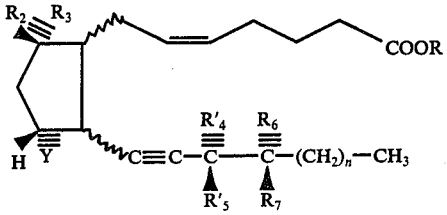

-continued wherein X is bromine, chlorine or iodine, and wherein $R_6$, $R_7$ and $n$ are as defined above, one of $R'_4$ and $R'_5$ is a hydroxy or a known protecting group bound to the chain by an ethereal oxygen atom, and the other is a hydrogen atom, Y is a hydroxy or a known protecting group bound to the ring by an ethereal oxygen atom, the lactol ring being in the trans-configuration with respect to the aliphatic side-chain, with a Wittig reagent comprising a group of formula —$(CH_2)_4$—COOR, wherein R is a hydrogen atom or a $C_1$-$C_{12}$ alkyl group, to give a compound of general formula (III)

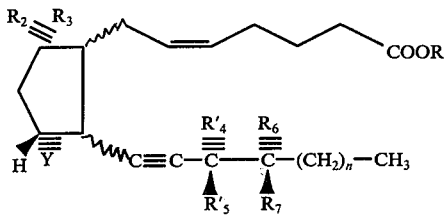

(III)

wherein R, Y, $R'_4$, $R'_5$, $R_6$, $R_7$ and $n$ are as defined above, and wherein one of $R_2$ and $R_3$ is a hydroxy group and the other is a hydrogen atom, and then deetherifying the resulting compound of formula (III) wherein Y is a known protecting group as defined above and/or one of $R'_4$ and $R'_5$ is a known protecting group as defined above and the other is a hydrogen atom, to give a compound of formula (I) wherein $R_1$ is a hydroxy group, one of $R_2$ and $R_3$ is a hydroxy group and the other is hydrogen, the symbol ---- is a single bond and one of $R_4$ and $R_5$ is a hydroxy group and the other is hydrogen, or if desired, oxidizing the 9-hydroxy group in the compound of formula (III) wherein Y is a known protecting group as defined above, and one of $R'_4$ and $R'_5$ is a known protecting group as defined above, and the other is a hydrogen atom, to give a compound of general formula (IV)

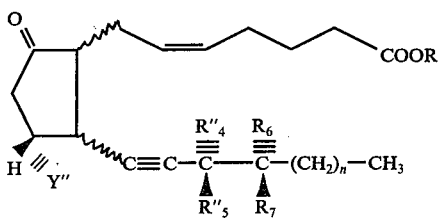

(IV)

wherein R, $R_6$, $R_7$ and $n$ are as above defined, Y" is a known protecting group as defined above, and one of $R''_4$ and $R''_5$ is a known protecting group, as defined above and the other is hydrogen, which, in turn, is deetherified in the 11- and 15- positions to give, according to the reaction conditions used, either a compound of general formula (I) wherein $R_2$ and $R_3$ together form an oxo group, the symbol ---- is a single bond and $R_1$ is hydroxy, or a compound of general formula (I) wherein $R_2$ and $R_3$ together form an oxo group, the symbol ---- is a double bond and $R_1$ is hydrogen, and then, if desired, reacting a compound of general formula (I) wherein R is a hydrogen atom, with a base to give a compound of general formula (I) wherein R is a cation, or esterifying a compound of general formula (I) wherein R is a hydrogen atom, to give a compound of general formula (I) wherein R is $C_1$-$C_{12}$ alkyl, or hydrolysing a compound of general formula (I) wherein R is a $C_1$-$C_{12}$ alkyl, to give a compound of general formula (I) wherein R is a hydrogen atom.

The hydrolysis of a compound of formula (I) wherein $R_2$ and $R_3$ together form an oxo group, and wherein R is a $C_1$-$C_{12}$ alkyl, to give a compound of formula (I) wherein $R_2$ and $R_3$ together form an oxo group and R is hydrogen, may be also carried out by enzymatic way, e.g. by using a yeast esterase.

In the compounds of formulae (II) to (IV), which may be either optically active or racemic compounds, the chains attached to the carbon atoms in the 8- position and in the 12- position are always in the trans-configuration.

The configuration of the lactol of formula (II) is the same as that of the lactol of formula (A).

When in the lactol of formula (II) B is

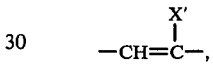

wherein X' is bromine, chlorine or iodine, the hydrogen atom linked to the carbon atom in the 13- position and the halogen atom linked to the carbon tom in the 14- position may be either in the transposition (geometric trans-isomers) or in the cis-position (geometric cis-isomers). Preferably they are in the trans-position. As hereabove stated, when the starting material used is the lactol of the above-reported formula (A') wherein X is the radical

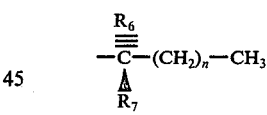

a nat-derivative of formula (III) is obtained, wherein $R_2$ is hydrogen and $R_3$ is a hydroxy group, while when the starting material used is the halo-lactol of the above-reported formula (A") wherein Z is as above defined, an ent-derivative of formula (III) is obtained, wherein $R_2$ is a hydroxy group and $R_3$ is hydrogen.

The reaction between the latol of formula (II) wherein R is -C| C- or

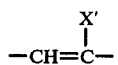

and X' is bromine or iodine with the Wittig reagent is carried out in the same conditions as the above reaction between the halo-lactol of formula (A) with the Wittig reagent.

When X' is chlorine, it is necessary, as starting above, to prolong the reaction time (up to 10 hours) when 1.5 to 2.5 moles of Wittig reagent are used per mole of lactol, while, by using shorter reaction times, for example 30 minutes, it is necessary to employ at least 5 moles of Wittig reagent per mole of lactol.

The oxidation of the 9-hydroxy group to yield an oxo group may be carried out with for example, Jones' reagent.

As stated above, the deetherification of the compound of formula (IV) may give according to the reaction conditions used, either a compound of general formula (I) wherein $R_2$ and $R_3$ together form an oxo group, the symbol ---- is a single bond and $R_1$ is hydroxy, or a compound of formula (I) wherein $R_2$ and $R_3$ together form an oxo group, the symbol ---- is a double bond, and $R_1$ is hydrogen.

The compound of formula (I) wherein $R_2$ and $R_3$ together form an oxo group, the symbol ---- is a single bond, and $R_1$ is hydroxy, is obtained, as the only product, by operating at 25° to 40° C, while operating at higher temperature, for example, at the reflux temperature for about 3 hours gives the compound of formula (I) wherein $R_2$ and $R_3$ together form an oxo group, the symbol ---- is a double bond and $R_1$ is hydrogen, as the only product. The other reaction conditions of the deetherification step are the same as above reported. The optional salification, esterification and saponification steps may be performed in a conventional manner, following the usual methods of organic chemistry.

The lactol of formula (II) wherein B is

and X' is bromine or iodine, may be prepared by the ame methods as described for the preparation of the lactol of formula (A), giving to the Z symbol the following meaning:

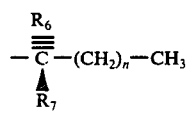

and replacing $R_a$ and $R_b$ by $R_4'$ and $R_5'$. The lactol of formula (II) wherein B is

may be prepared starting from the lactone of formula (Q) wherein Z has the following meaning:

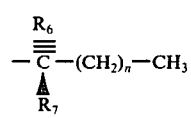

by reaction with a halogenating agent, such as for example, a sulphonyl chloride, preferably $SO_2Cl_2$, so obtaining a lactone of formula:

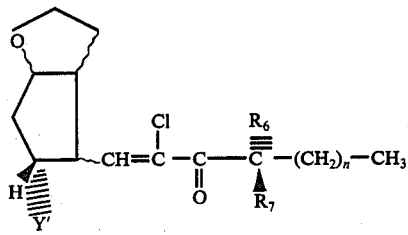

wherein Y', $R_6$ and $R_7$ are as above defined

In the compound resulting from the halogenation, the hydrogen atom linked to the carbon atom in the 13- position and the halogen atom linked to the carbon atom in the 14- position may be either in the trans-position (geometric trans-isomers: 92–95%) or in the cis-position (geometric cis-isomers: 5–8%). The reaction may be performed in a solvent preferably selected from the group consisting of pyridine, acetone, acetic acid, toluene, diethylether, benzene, water or their mixtures - and then, by proceeding as indicated at pages 7,8, and 9 of the present specification with respect to the compounds wherein X is bromine or iodine. The same lactone of the immediately preceding formula may be obtained also by reaction of the aldehyde of formula (H) with the phosphonate of formula:

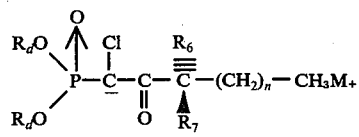

wherein $R_d$, $R_6$, $R_7$ and M $^{(+)}$ are as above defined.

Also in this case, a little percentage of geometric cis-isomers (5–8%) is obtained. The chloro-phosphonate carbanion salt of the above formula may be obtained from the corresponding non-halogenated carbonion salt by treatment with e.g. N-chloroacetamide or N-chlorosuccinimide. The lactol of formula (II) wherein B is —C|C— may be prepared by dehydrohalogenation of the lactol of formula (II) wherein B is

by means of a base, for example potassium tert.butylate or methylsulphinylcarbanion in an organic solvent such as dimethylsulphoxide.

It is evident that, for economic reasons, in the lactol of formula (II), B is preferably a

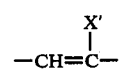

group, since both the dehydrohalogenation and the alkylation with the Wittig reagent take place at the same time, in an only one step. When in the lactol of formula (II) B is

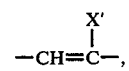

wherein X' is bromine, chlorine or iodine, during the reaction with the Wittig reagent, the dehydrohalogenation takes place as easily when the hydrogen atom linked to the carbon atom in the 13- position and the halogen atom linked to the carbon atom in the 14- position are in the trans-position as when they are in the cis-position.

Also the Wittig reagent comprising a group of formula —$(CH_2)_4$—COOR, may be prepared as hereabove described.

Among the intermediates described in this specification, the following are compounds of the invention:
1. the phosphonates of formula

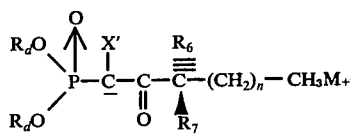

wherein X', $R_d$, $R_6$, $R_7$ and $M^{(+)}$ are as above defined;
2. the lactol of formula

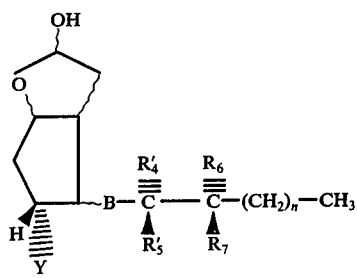

wherein Y, B, $R'_4$, $R'_5$, $R_6$, $R_7$ and $n$ are as above defined;
3. the lactone of formula

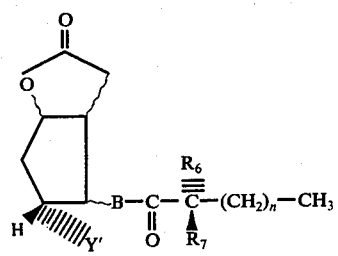

wherein Y', B, $R_6$, $R_7$ and $n$ are as hereabove defined;
4. a compound of formula

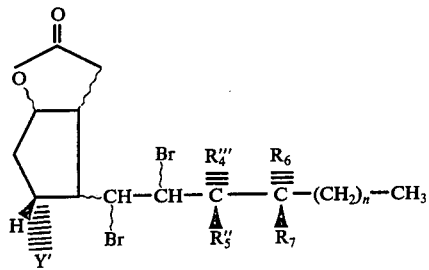

wherein Y', $R_6$, $R_7$ and $n$ are as above defined, and one of $R_4'''$ and $R_5'''$ is hydroxy and the other is hydrogen, or $R_4'''$ and $R_5'''$ together form an oxo group;
5. a compound of formula

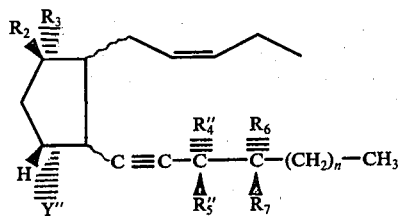

wherein one of $R_2$ and $R_3$ is hydrogen and the other is hydroxy or $R_2$ and $R_3$ together form an oxo group, R is hydrogen or $C_1$- $C_{12}$ alkyl, Y'', R''$_4$, R''$_5$, $R_6$, $R_7$ and $n$ are as defined above.

All the intermediates mentioned under the foregoing points 1) to 5) are optically active or racemic compounds.

The new prostaglandin derivatives of formula (I) may be used for the same therapeutical indications as natural prostaglandins, with respect to which, however, they offer the advantage of being no substrates for the enzyme 15-prostaglandin dehydrogenase, which, as is known, quickly inactivates natural prostaglandins, and, furthermore, are characterized by a more selective therapeutical action.

Pharmacological tests have for example shown that the compound 16S-methyl-13,14-dehydro-ent-11,15-epi-PGE$_2$ has an excellent spasmogenic activity in vitro in the uterus of rate, while it is practically devoid of any activity in vitro in the stomach of rats and in the ileum of guinea-pigs.

The rat uterus test consisted of a 10 ml thermostatic bath held at 29° C, in which oestrogenized rat uteri under 0.5 g traction were carboxygenated in a Dejalon saline solution. The preparation was left to stbilize for 30 minutes before the compounds and the standard were tested. Response was measured using a isotonic frontal lever, long enough to amplify the response 4.5 times.

The guinea pig eleum test consisted of a 10 ml thermostatic bath held at 35° C, containing the ileum of a male guinea pig, under 0.5 g traction, carboxygenated in a Tyrode solution; this was left for 30 minutes to stablize before the compounds were tested. The response was recorded using a isotonic frontal lever, long enough to amplify the response 4.5 times Both the compound 16S-methyl-13,14-dehydro-PGE$_2$ and the compound 16R-methyl-13,14-dehydro-PGE$_2$ show to have a very good anti-bronchospastic activity when tested in vivo and in vitro in guinea-pigs, if compared with the natural PGE$_2$ (histamine- and anaphylactic shock- induced bronochospasm), with respect to which they are four to six times more active, and are therefore useful in the treatment of asthma.

Antibronchospastic (anti-asthmatic) activity was determined in guinea-pigs divided into groups, and treated with a histamine spray (0.2% aqueous solution of histamine hydrochloride): the time when the animal showed bronchospasm was then recorded. Four hours later, the same animals were treated with a spray of the test compounds at different solutions in saline, and with a spray of standard PGE$_2$ solution. They were then given another histamine spray (0.2%) and again, the times taken for bronchospasm to appear were noted.

Moreover, the compounds of the present invention are endowed with an excellent anti-ulcer activity as well as with a strong gastric anti-secretory effect, as shown by the following Tables: where the conventional value of 1 is given to the anti-ulcer and anti-secretory activity of $PGE_2$, and where the compounds of the invention are compared also with 13,14-dehydro-$PGE_2$, 16S-methyl-$PGE_2$ and 16(S,R)-methyl-13,14-dehydro-$PGE_2$.

| INHIBITION OF STRESS-INDUCED GASTRIC ULCERS IN RATS (*) | | | | |
|---|---|---|---|---|
| | Potency Ratio (Fiducial Limits For P=0.05) | | $ED_{50}$ (**) (Fiducial Limits For P=0.05) | |
| Prostaglandin | Subcutaneously | os | Subcutaneously | os |
| $PGE_2$ | 1 | 1 | 118.8(116.9–120.7) | 717.0(677.0–760.8) |
| 13,14-dehydro-$PGE_2$ | 4.9(2.4–9.6) | 9.3(4.5–19.0) | 43.0(34.3–56.9) | 63.0(54.4–73.3) |
| 16S-methyl-$PGE_2$ | 12.8(9.0–17.9) | 39.0(18.9–80.3) | 17.7(16.2–19.4) | 24.2(17.7–35.4) |
| 16(S,R)-methyl-13,14-dehydro-$PGE_2$ | 30.8(20.4–44.2) | 39.8(17.1–102.1) | 3.41(2.81–3.91) | 20.2(14.1–26.8) |
| 16S-methyl-13,14-dehydro-$PGE_2$ | 69.8(46.4–105.2) | 42.8(18.8–101.7) | 0.9(0.8–1.0) | 15.0(12.9–17.4) |
| 16R-methyl-13,14-dehydro-$PGE_2$ | 43.1(28.4–64.6) | 105.6(46.6–282.6) | 1.5(1.4–1.6) | 9.8(6.6–13.4) |
| 16S-methyl-13,14-dehydro-15-epi-$PGE_2$ | 2.9(1.9–4.5) | 3.8(1.75–8.4) | 91.1(82.9–100.9) | 220.4(187.3–261.1) |
| 16R-methyl-13,14-dehydro-15-epi-$PGE_2$ | 7.4(4.8–11.1) | 7.3(3.1–16.9) | 8.7(8.1–9.5) | 141.2(101.0–225.3) |

(*) The ulcers are induced according to the method of Takagi-Okabe (K. Takagi et al., Jap. J. Pharmacol., 18, 9 (1968)
(**) Expressed in μg/kg

| ANTISECRETORY ACTIVITY IN RATS (*) | | |
|---|---|---|
| | Potency Ratio (Fiducial Limits For P = 0.05) | $ED_{50}$ (**) (Fiducial Limits For P = 0.05) |
| Prostaglandin | Subcutaneously | Subcutaneously |
| $PGE_2$ | 1 | 155.4 (144.7–166.3) |
| 13,14-dehydro-$PGE_2$ | 2.6 (1.4–4.5) | 55.0 (46.0–65.8) |
| 16S-methyl-$PGE_2$ | 13.5 (7.9–23.7) | 11.2 (7.9–14.5) |
| 16(S,R)-methyl-13,14-dehydro-$PGE_2$ | 28.2 (18.1–41.6) | 6.8 (4.8–8.8) |
| 16S-methyl-13,14-dehydro-$PGE_2$ | 35.7 (20.8–68.9) | 4.2 (2.2–6.2) |
| 16R-methyl-13,14-dehydro-$PGE_2$ | 48.3 (33.5–71.6) | 2.6 (2.4–2.8) |
| 16R-methyl-13,14-dehydro-15-epi-$PGE_2$ | 3.8 (2.7–5.5) | 32.8 (31.3–34.5) |

(*) The antisecretory activity was studied according to H. Shay et al., Gastroenter., 26, 906 (1954)
(**) Expressed in μg/kg In the Tables it has to be noted that the 15S-hydroxy derivatives (either the 16S-methyl derivative or the 16R-methyl derivative) are provided with a higher activity than the reference compounds as well as the Tables show the activities surprisingly owned by the 15R-hydroxy derivatives (i.e. the 16S-methyl-13,14-dehydro-15-epi-$PGE_2$ and the corresponding 16R derivative), in that, as is known, the 15R-hydroxy derivatives of prostaglandins have up to now proven to be generally inactive in the pharmacological tests of the various Authors.

The compounds of general formula (I) can be administered orally, parenterally or intravenously, by rectal suppositories or by inhalation. For example, they can be administered by intravenous infusion of a sterile isotonic saline solution at the rate of 0.01 to 10, preferably 0.05 to 1, μg/kg of mammal body weight per minute. The invention therefore also provides a pharmaceutical composition comprising a compound of general formula (I) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions. Examples of substances which can serve as carriers or diluents are water, gelatin, lactose, starches, magnesium stearate, talc, vegetable oil, benzyl alcohol and cholesterol.

The invention is illustrated by the following examples wherein the abbreviations THP, DIOX, THF, DMSO, PHT, and DIBA refer to tetrahydropyranyl, dioxanyl, tetrahydrofuran, dimethylsulphoxide, pyrrolidone-2-hydrotribromide and diisobutylaluminium-hydride, respectively.

EXAMPLE 1

A solution of 0.26 g of dl-5β-hydroxymethyl-2α,4α-dihydroxycyclopentane-1α-acetic acid-γ-lactone-4-acetate in 8 ml of dichloromethane was added all at once to a solution of pyridine-chromic anhydride complex prepared from 0.8 g of $CrO_3$ and 1.34 ml of anhydrous pyridine in 23 ml of dichloromethane. After stirring for 15 minutes, it was diluted with 50 ml of benzene. The organic phase was washed with 7 ml of 40% citric acid and then 5 times with 3 ml each of a saturated solution of ammonium sulfate, then it was dried and concentrated to give a solution of about 0.25 g of dl-5β-formyl-2α,4α-dihydroxycyclopentane-1α-acetic acid-γ-lactone-4-acetate in 10 ml of benzene.

A solution of 0.31 ml of dimethyl-(2-oxo-heptyl)phosphonate in 4 ml of benzene was added dropwise to a suspension of 43 mg of 80% sodium hydride in 5 ml of dry benzene until there was no more evolution of hydrogen. An hour afterwards, 0.255 g of N-bromosuccinimide was added and the mixture stirred for 15 minutes, giving the carbanion of dimethyl-(1-bromo-2-oxoheptyl)-phosphonate. The aldehyde was then added and stirring continued for another 15 minutes. The organic phase was washed with water, a 5% aqueous solution of $NaH_2PO_4$, and again with water until the washing were neutral, and the organic phase was evaporated to dryness. The residue, 0.6 g, was chromatographed on 20 g of silica gel to give 0.335 g of dl-5β-(2'-bromo-3'-oxo-oct-1'-trans-1'-enyl)-2α,4α-dihydroxycyclopentane-1α-acetic acid-γ-lactone-4-acetate, m.p. 121°–123° C; $\lambda_{max}^{MeOH}$ 241 mμε= 11,700 (72% yield), by elution with benzene-ethyl ether (90 : 10).

EXAMPLE 2

At room temperature, a solution of 7.04 g(0.02moles) of 5β-hydroxymethyl-2α,4α-dihydroxycyclopentane-1α-acetic acid-γ-lactone-4-p-phenylbenzoate in 25% DMSO in benzene (100 ml) was treated with dicyclohexylcarbodiimide (12.5 g) and pyridine trifluoroacetate (1 ml) in 25 ml of 25% DMSO in benzene.

The mixture was stirred for 4 hours at room temperature and then diluted with a solution of oxalic acid (5.46 g) in methanol (30 ml), to destroy the excess carbodiimide. After an additional 45 minutes of stirring the reaction mixture was diluted with water (100 ml) and benzene (150 ml). The precipitate was removed by filtration and the organic phase was evaporated and washed with water until neutral, then dried on $MgSO_4$ and evaporated down to about 30 ml, giving a solution of about 0.02 moles of 5β-formyl-2α,4α-dihydroxy-cyclopentane-1α-acetic acid-γ-lactone-4-p-phenylbenzoate.

Under inert gas, a solution of 5.67 g of dimethyl-(2-oxo-3S-methylheptyl)-phosphonate [b.p. 105°–110° C; $[α]_D$ = +20.3 $[α]_{365°}$= +114.3° ($CHCl_3$)] in benzene (20 ml) was added dropwise to a stirred suspension of 0.72 g of 80% sodium hydride (NaH), in 90 ml of benzene.

When there was no longer any evolution of hydrogen (about 1 hour), 4.28 g of N-bromo-succinimide was added and the mixture stirred for 30 minutes, to give a solution of the carbanion of dimethyl-(1-bromo-2-oxo-3S-methylheptyl)-phosphonate, sodium salt, to which the above prepared aldehyde solution was added.

After an additional stirring for 20 minutes, the reaction mixture was diluted with water the organic layer washed with 10% $NaH_2PO_4$ and then with water until neutral, dried on $Na_2SO_4$ and evaporated to dryness. The residue (14 g) was chromatographed on silica gel (280 g) to yield, by elution with methylene chloride, 7.42 g of 5β-(2'-bromo-3'-oxo-4'S-methyl-oct-1'-trans-1'-enyl)-2α,4α-dihydroxycyclopentane-1α-acetic acid-γ-lactone-4-p-phenylbenzoate, m.p. 72°–74° C; $[α]_D$ = −113° (chloroform).

EXAMPLE 3

Working in dry conditions and in the dark to a stirred suspension of the sodium salt of dimethyl-(2-oxo-heptyl)phosphonate in dry dimethoxyethane (prepared from 43 mg of 80% NaH and 0.31 ml of phosphonate, under the conditions described in Example 1), 0.355 g of bromodioxane in 3 ml of dimethoxyethane was added. It was stirred for 10 minutes, then another 43 mg of 80% NaH was added and stirring continued for 20 minutes longer, until no more hydrogen was evolved. After addition of 1.2 × $10^{-3}$ moles of dl-5β-formyl-2α, 4α-dihydroxycyclopentane-1α-acetic acid-γ-lactone-4-acetate and working up the reaction mixture as described in Example 1, 185 mg of dl-5β-(2'-bromo-3'-oxo-oct-1'-trans-1'-enyl)-2α,4α-dihydroxycyclopentane-1α-acetic acid-γ-lactone-4-acetate was obtained (λ max at 250 mμ ε = 10,050).

EXAMPLE 4

A solution of dimethyl-(2-oxo-octyl)-phosphonate (3.24 g) in 8 ml of benzene was added to a suspension of 0.415 g of 80% NaH (dispersion in mineral oil) in 60 ml of benzene. Stirring was continued until no more hydrogen was evolved, then 1.9 g of N-bromoacetamide was added to generate the carbanion of dimethyl-(1-bromo-2-oxo-octyl)-phosphonate. Stirring was continued for 45 minutes, then a solution of 4 g of 5β-formyl-2α,4α-diol-cyclopentane-α-acetic acid-γ-lactone-4-p-phenylbenzoate prepared by one of the two methods outlined in Examples 1 and 2 was added.

After 20 minutes the reaction mixture was filtered and the organic phase was washed with water, 5% $NaH_2PO_4$, and water again, dried on $MgSO_4$ and evaporated to dryness. The residue was crystallized from ethyl ether to give 3.25 g of 5β-(2'-bromo-3'-oxo-non-1'-trans-1'-enyl)-2α,4α-dihydroxycyclopentane-1α-acetic acid-γ-lactone-4-phenylbenzoate, m.p. 137°–140° C, $[α]_D$ = −102° ($CHCl_3$), $[α]_{365°}$ = −514° ($CHCl_3$).

Found %: C 64.66; H 5.84; Br 14.88; Calc. %: C 64.56; H, 5.78; Br 14.81.

EXAMPLE 5

Starting with 4 g of 5β-formyl-2α,4α-dihydroxycyclopentane-1α-acetic acid-γ-lactone-4-p-phenylbenzoate, reaction with the sodium salt of dimethyl-(2-oxooctyl)-phosphonate (1.2 equivalents) in benzene yielded 4.2 g of 5β-(3'-oxo-non-trans-1'-enyl)-2α,4α-dihydroxycyclopentane-1α-acetic acid-γ-lactone-p-phenylbenzoate, m.p. 60°–61°; $[α]_D$ = −145° ($CHCl_3$).

A solution of this compound in anhydrous ethyl ether (37 ml) was added dropwise to a stirred 0.05M $Zn(BH_4)_2$ solution in ether (200 ml).

After 15 minutes, the reduction of the trans-enone lactone was complete and the excess reagent was decomposed by addition of a saturated NaCl solution and 2N HCl. The organic phase was separated, washed until neutral, dried and evaporated to dryness to afford a crude mixture of the two 3'S and 3'R epimeric alcohols: 5β-(3'}-hydroxy-non'-trans-1'-enyl)-2α,4α-dihydroxycyclopentane-1α-acetic acid-γ-lactone-p-phenylbenzoate (4.2 g). After anhydrification with benzene this product was dissolved in dry THF (60 ml) and treated with 9.95 g of pyrrolidone hydrotribromide (PHT). The reagent dissolved completely. After standing overnight with stirring, the pyrrolidone hydrobromide which was formed in the reaction precipitated and was filtered out. The organic phase was diluted with benzene, washed with saturated NaCl solution until neutral, dried and evaporated to dryness. The resulting crude 5β-(1',2'-dibromo-3'-hydroxynonyl)-2α,4α-dihydroxy-cyclopentane-1α-acetic acid-γ-lactone-4-p-phenylbenzoate (6.1 g) was dissolved in 220 ml of acetone. The solution was cooled to −5° and over a period of 5 minutes 11.2 ml of Jones' reagent was added. It was left at −5° for another 8 minutes, then diluted with 7 vol. of benzene. The organic phase was washed with saturated ammonium sulfate solution until neutral and dried over $MgSO_4$ to give a benzene-acetone solution of 5β-(1'}, 2'}-dibromo-3'-oxo-nonyl)-2α,4α-dihydroxycyclopentane-1α-acetic acid-γ-lactone-4-p-phenylbenzoate. To this solution, from which the product was not isolated, 3.3 ml of triethylamine were added and the solution left to stand for 8 hours at room temperature.

The benzene phase was washed with citric acid, water, saturated $NaHCO_3$, and water. It was dried over $Na_2SO_4$ and evaporated to dryness, giving 4.3 g of the crude bromoketone. After crystallization from ethyl ether, 2.3 g of 5β-(2'-bromo-3'-oxo-non-1'-trans-1'-enyl)-2α,4α-dihydroxycyclopentane-1α-acetic acid-γ-lactone-4-p-phenylbenzoate were obtained, m.p. 138°–140°; $[α]_D$= −102.5° ($CHCl_3$).

EXAMPLE 6

A solution of 5β-(2'-bromo-3'-oxo-non-1'-trans-1'-enyl)-2α,4α-dihydroxy-cyclopentane-1α-acetic acid-γ-lactone-4-p-phenylbenzoate (3.5 g) in DME (80 ml) was added dropwise to a stirred 0.05 M $Zn(BH_4)_2$ solution in ether (300 ml). After 20 minutes the excess reagent was decomposed with 2N $H_2SO_4$ and a saturated solution of NaCl. The organic phase was separated and washed until neutral with saturated NaCl, dried and evaporated to dryness. The residue was chromatographed on 750 g of SiO$_2$, using dichloromethane as eluent, to give 2.24 g of 5β-(2'-bromo-3'S-hydroxy-non-1'-trans-1'-enyl)-2α,4α-dihydroxycyclopentane-1α-acetic acid-γ-lactone-4-p-phenylbenzoate; $[\alpha]_D = -63°$; $[\alpha]_{365°} = -306°$ and 1.23 g of the 3'R-hydroxy isomer, with m.p. 97°-99° (from isopropyl ether) $[\alpha]_D = -83°$; $[\alpha]_{365°} = -373°$.

A stirred solution of the 3'S-hydroxy-p-phenylbenzoate isomer (2.2 g) in 30 ml of dry methanol was treated with 620 mg of anhydrous K$_2$CO$_3$.

After 2 hours, it was neutralized with 15% aqueous acetic acid, then concentrated under vacuum to a small volume, and taken up again in benzene. The organic phase was washed until netural and then evaporated to dryness to give the crude 5β-(2'-bromo-3'S-hydroxy-non-1'-trans-1'-enyl)-2α,4α-dihydroxy-cyclopentane-1α-acetic acid-γ-lactone (1.45 g) which was dissolved in anhydrous benzene and reacted at room temperature with 1.45 ml of 2,3-dihydropyran and 15 mg of p-toluenesulfonic acid.

After 2 hours, the benzene phase was washed with 5% aqueous KHCO$_3$, then water, dried and concentrated to a small volume. The residue was chromatographed on silica gel to give, by elution with cyclohexane and cyclohexane-ethylacetate mixtures, 2.1 g of 5β-(2'-bromo-3'S-hydroxy-non-1'-trans-1'-enyl)-2α,4α-dihydroxycyclopentane-1α-acetic acid-γ-lactone-4,3'-bis-THP-ether, an oil, $[\alpha]_D = -16.9$; $[\alpha]_{365°} = -38.8°$ (CHCl$_3$).

In the same way, starting from the 3'R isomer the 5β-(2'-bromo-3'R-hydroxy-non-1'-trans-1'-enyl)-2α,4α-dihydroxycyclopentane-1α-acetic acid-γ-lactone-3',4-bis-THP-ether, oil, $[\alpha]_D = +16.9°$; $[\alpha]_{365°} = +56.6°$ (CHCl$_3$) was prepared.

EXAMPLE 7

A solution of 1.5 g of 5α-hydroxymethyl-2β,4α-dihydroxycyclopentane-1β-acetic acid-γ-lactone-4-p-phenylbenzoate in 22 ml of benzene-DMSO (75:25) was treated at room temperature and stirred for 3 hours with 2.66 g of dicyclohexylcarbodiimide and 4.35 ml of a solution of pyridine tricluoroacetate in benzene-DMSO (75:25) prepared by diluting 1 ml of trifluoroacetic acid and 2 ml of pyridine to 25 ml with benzene-DMSO (75:25).

The excess reagent was destroyed by addition of a solution of oxalic acid dihydrate 1.62 g, in methanol (3.5 ml). After 30 minutes, the reaction mixture was diluted with water (58 ml) and benzene (25 ml), and filtered.

The organic phase was washed until neutral, dried on Na$_2$SO$_4$, then concentrated to a small volume, affording a benzene solution of approximately 1.5 g of 5α-formyl-2β,4α-dihydroxy-cyclopentane-1β-acetic acid-γ-lactone-4-p-phenylbenzoate, m.p. 158°-160° $[\alpha]_D = -18.6°$ (CHCl$_3$) (named aldehyde solution).

To a benzene suspension of 194 mg of 80% NaH in mineral oil, a solution of 1.62 g of dimethyl-(2-oxo-octyl)-phosphonate in 5 ml of benzene was added dropwise and continually stirred until there was no more evolution of hydrogen. The 1.24 g of N-bromo-caprolactam were added to form the carbanion of dimethyl-(1-bromo-2-oxo-octyl)-phosphonate. After 15 minutes the solution of the aldehyde, prepared as described above, was added and the reaction mixture stirred for 15 minutes.

The organic phase was filtered and washed with 5% NaH$_2$PO$_4$ and water until neutral, evaporated to dryness.

The residue was chromatographed on silica gel to give by elution with cyclohexane-ethylacetate (80:20) 1.1 g of 5α-(2'-bromo-3'-oxo-non-1'-trans-1'-yl)-2β,4α-dihydroxycyclopentane-1β-acetic acid-γ-lactone-4-p-phenyl-benzoate, m.p. 108°-109°.

In similar way, using bromo-succinimide as brominating agent and a phosphonate selected from the group consisting of:
dimethyl-(2-oxo-heptyl)-phosphonate;
dimethyl-(2-oxo-3S-methylheptyl)-phosphonate;
dimethyl-(2-oxo-3S-methyloctyl)-phosphonate and
dimethyl-(2-oxo-nonyl)-phosphonate instead of the
dimethyl-(2-oxo-octyl)-phosphonate the following α-bromo-α,β-unsaturated ketone-4-p-phenylbenzoates:

α,β-unsaturated ketone-4-p-phenylbenzoates:
5α-(2'-bromo-3'-oxo-oct-1'-trans-1'-enyl)-2β,4α-dihydroxycyclopentane-1β-acetic acid-γ-lactone (1'H 6.94δ $J_{AB} = 9$ Hz);
5α-(2'-bromo-3'-oxo-3'S-methyl-oct-1'-trans-1'-enyl)-2β,4α-dihydroxy-acid-γ-lactone (1'H 6.91 δ $J_{AB} = 9$ Hz); 5α-(2'-bromo-3'-oxo-4'-methyl-non-1'-trans-1'-enyl)-2β,4α-dihydroxy-acid-γ-lactone (1'H 6.92 δ $J_{AB} = 9$ Hz);
5α-(2'-bromo-3'-oxo-non-1'-trans-1'-enyl)-2β,4α-dihydroxy-acid-γ-lactone (1'H 6.94 δ $J_{AB} = 9$ Hz), m.p. 108°-109° C;
5α-(2'-bromo-3'-oxo-dec-1'-trans-1'-enyl)-2β,4α-dihydroxy-acid-γ-lactone (1'H 6.92δ $J_{AB} = 9$ Hz) were prepared.

EXAMPLE 8

A solution of 3.72 g of 5β-(3'-oxo-4'-S-methyl-oct-1'-trans-1'-enyl)-2α,4α-dihydroxycyclopentane-1α-acetic acid-γ-lactone-4-p-phenylbenzoate [m.p. 105°, $[\alpha]_D = -129°$ (CHCl$_3$)]in 75 ml of methanol was added dropwise to a solution of 290 mg of NaBH$_4$ in 30 ml of methanol, cooled to $-15°$ C, at a rate such that the temperature of the reaction mixture was maintained between $-8°$ and $-5°$ C. After standing for 30 minutes at $-5°$ C, it was neutralized by addition of 25% aqueous acetic acid and the methanol evaporated off under vacuum. The residue was taken up in dichloroethane, washed until neutral, dried and evaporated to dryness.

The residue (3.7 g) of 5β-(3'{-hydroxy-4'S-methyl-oct-1'-trans-1'-enyl)-2α,4α-dihydroxy-1α-acetic acid-γ-lactone-4-p-phenylbenzoate (a mixture of the two isomeric alcohols: 3'S and 3'R), after azaetropic water removal with benzene was dissolved in 55 ml of dry THF and treated with 8.8 g of pyrrolidone-2-hydrotribromide (PHT) overnight, under stirring. The precipitate which formed was separated out, washed with ethyl ether, which was added back to the organic phase. The combined organic phases were washed with a saturated solution of ammonium sulfate until neutral, then evaporated to dryness to give 5 g of 5β-(1',2'-dibromo-3'{-hydroxy-4'S-methyl-octan-1'-yl)-2α,4α-dihydroxy-cyclopentane-1α-acetic acid-γ-lactone-p-phenylbenzoate.

A solution of this crude product in 42 ml of benzene-DMSO 75:15 was treated with 5 g of dicyclohexylcarbodiimide and 7.26 ml of a solution of pyridine trifluoroacetate in benzene-DMSO 75:25. After 3 hours the excess reagent was destroyed by adding a solution of 3.18 g of oxalic acid dihydrate in 7 ml of methanol. This was stirred for 30 minutes at room temperature then diluted with water and benzene. After filtration on the organic phase was separated, washed with water until neutral and evaporated to dryness to give 4.8 g of crude 5β-(1',2'}-dibromo-3'-oxo-4'S-methyl-octan-1'-yl)-2α,-4α-dihydroxycyclopentane-1α-acetic acid-γ-lactone-p-phenylbenzoate. A solution of this compound in dry benzene (30 ml) was treated with dry pyridine (2.5 ml) for 8 hours at room temperature. Then the organic phase was washed with 40% citric acid, water, sodium bicarbonate and water again until neutral, then it was evaporated to a small volume. The residue was chromatographed on silica gel and after elution with methylene chloride, 1.98 g were obtained of 5β-(2'-bromo-3'-oxo-4'S-methyl-oct-1'-trans-1'-enyl)-2α,4α-dihydroxycyclopentane-1α-acetic acid-γ-lactone-p-phenyl-benzoate, m.p. 71°-73° C.

A solution of this compound in methanol was added dropwise to a solution of 400 mg of $NaBH_4$ in 30 ml of methanol, precooled to −15° C. It was maintained at this temperature for 30 minutes and then neutralized with 15% aqueous acetic acid, evaporated to dryness and the residue chromatographed on 250 g of silica gel. Elution with methylene chloride gave 1.3 g of 5β-(2'-bromo-3'S-hydroxy-4'S-methyl-oct-1'-trans-1'-enyl)-2α,4α-dihydrocyclopentane-1α-acetic acid-γ-lactone-4-p-phenylbenzoate $[\alpha]_D = -74.6°$, $[\alpha]_{365°} = 338°$ ($CHCl_3$); and 0.38 g of 5β-(2'-bromo-3'R-hydroxy-4'S-methyl-oct-1'-trans-1'-enyl)-2α,4α-dihydroxycyclopentane-1α-acetic acid-γ-lactone-4-p-phenylbenzoate, $[\alpha]_D = -91.6°$, $[\alpha]_{365°} = -416°$ ($CHCl_3$).

EXAMPLE 9

To a suspension of 0.31 g of NaH in dry benzene was added dropwise a solution of 2.65 g of dimethyl(2-oxo-3'R-methylheptyl)-phosphonate [b.p. = 122–126°/1 mm Hg, $[\alpha]_D = 20.5°$; $[\alpha]_{365°} = -114°$ ($CHCl_3$)]. The mixture was stirred for one hour, until no more hydrogen was evolved. Then 1.83 g of N-bromo-succinimide was added, to form the carbanion of dimethyl-(1-bromo-2-oxo-3'R-methylheptyl)-phosphonate sodium salt. Stirring was continued for 15 minutes, then a solution of 3 g of 5β-formyl-2α,4α-dihydroxycyclopentane-1α-acetic acid-γ-lactone-p-phenylbenzoate in 20 ml of benzene was added.

After 25 minutes it was filtered and the organic phase washed with 5% $NaH_2PO_4$, then water again until neutral and evaported to dryness. The residue was chromatographed on 80 g of silica gel and eluted with methylene chloride to give 2.22 g of 5β-(2'-bromo-3'-oxo-4'-R-methyl-oct-1'-trans-1'-enyl)-2α,4α-dihydroxycyclopentane-1α-acetic acid-γ-lactone-p-phenylbenzoate which was crystallized from methanol, m.p. 110°–111° C, $[\alpha]_D = -108°$ C ($CHCl_3$).

In the same way, starting with one of the 4-esters (formate, acetate, propionate, p-phenylbenzoate) of the 5β-formyl-2α,4α-dihyroxycyclopentane-1α-acetic acid-γ-lactone, one of the 4-esters (in particular, the 4-p-phenylbenzoate) of the following 2α,4α-dihydroxycyclopentane-1α-acetic acid-γ-lactones:

5β-(2'-bromo-3'-oxo-4'S-methyl-non-1'-trans-1'-enyl);
5β-(2'-bromo-3'-oxo-4'R-methyl-non-1'-trans-1'-enyl);
5β-(2'-bromo-3'-oxo-4'S,R-methyl-non-1'-trans-1'-enyl);
5β-(2'-bromo-3'-oxo-4'S,R-methyl-oct-1'-trans-1'-enyl);
5β-(2'-bromo-3'-oxo-dec-1'-trans-1'-enyl);
5β-(2'-bromo-3'-oxo-4'S,R-methyl-dec-1'-trans-1'-enyl);
5β-(2'-bromo-3'-oxo-oct-1'-en-1'-enyl), were prepared.

The structures were characterized by NMR spectra: 1'H (proton) 6.92 – 6.96 δ (d) $J_{AB} = 9$ Hz.

EXAMPLE 10

A solution of 3.8 g of 5β-(3'-oxo-4'R-methyl-oct-1'-trans-1'-enyl)-2α,4α-dihydroxycyclopentane-1α-acetic acid-γ-lactone-p-phenylbenzoate (m.p. 75–77°; $[\alpha]_D = -152°$) in methanol was added dropwise to a precooled solution (−15°) of 0.8 g of $NaBH_4$ in methanol. After stirring for 15 minutes a saturated solution of $NaH_2PO_4$ was poured to decompose the excess reagent, then it was extracted with $CHCl_3$ to obtain 3.82 g of 5β-(3'-hydroxy-4'R-methyl-oct-1'-trans-1'-enyl)-2α,4α-dihydroxycyclopentane-1α-acetic acid-γ-lactone-p-phenylbenzoate (a mixture of the two epimeric 3'S and 3'R alcohols).

Three grams of this mixture, dried over benzene, were dissolved in 45 ml of anhydrous THF and treated with 7.13 g of PHT, overnight at room temperature.

The solid which separated out after dilution with ethyl ether was filtered and the filtrate washed until neutral with a saturated solution of $(NH_4)_2SO_4$ and water, then evaporated to dryness. The 4.05 g of 5β-(1',2'-dibromo-3'-hydroxy-4'-R-methyl-oct-1'-trans-1'-enyl)-2α,4α-dihydroxycyclopentane-1α-acetic acid-γ-lactone-4-p-phenylbenzoate were dried over benzene and dissolved in 35 ml of benzene-DMSO 75:15, then 4.05 g of dicyclohexyl carbodiimide and 6.6 ml of a solution of pyridine trifluoroacetate in benzene:DMSO 75:25 were added.

After 3 hours at room temperature, the excess reagent was decomposed by addition of a solution of 2.47 g of oxalic acid dihydrate in 5.4 ml of methanol. The reaction mixture was partitioned between 90 ml of water and 45 ml of benzene, filtered, the organic phase washed until neutral, dried and evaporated to dryness to give 4.1 g of crude 5β-(1',2'-dibromo-3'-oxo-4'R-methyl-oct-1'-trans-1'-enyl)-2α,4α-dihydroxycyclopentane-1α-acetic acid -γ-lactone-4-p-phenylbenzoate. This product was dissolved in benzene and treated with 1.68 g of anhydrous triethylamine for 6 hours at room temperature. It was then washed with 40% aqueous citric acid and then with water until neutral and evaporated to dryness, yielding 3.5 g of crude 5β-(2'-bromo-3'-oxo-4'-R-methyl-oct-1'-trans-1'-enyl)-2α,4α-dihydroxycyclopentane-1α-acetic acid-γ-lactone-p-phenylbenzoate.

After crystallization, 2.6 g of product were obtained with a melting point of 107°–110° C.

The same compound was obtained by treatment of 5β-(3'-oxo-4'R-methyl-oct-1'-trans-1'-enyl)-2α,4α-dihydroxycyclopentane-1α-acetic acid-γ-lactone (2.3 g, 0.5 × 10⁻³M) in dry THF (30 ml) with pyrrolidone hydrotribromide (2.85 g, 0.5 × 10⁻³M) at room temperature for 3 hours. After dilution with anhydrous ether and removal of the pyrrolidone hydrobromide by filtration, the organic layer was washed until neutral with a saturated aqueous solution of $(NH_4)_2SO_4$ and dried over $Na_2SO_4$.

The organic solvents were removed in vacuo, yielding 3.42 g of crude 5β-(3'-oxo-1',2'-dibromo-4'R-methyl-octan-1'-yl)-2α,4α-dihydroxycyclopentane-1α-acetic acid-γ-lactone, which was dissolved in 15 ml of a anhydrous benzene and then treated with 0.1 g of dry pyridine at room temperature for 3 hours.

The reaction mixture was diluted with benzene, washed with 1N $H_2SO_4$, water, 5% $NaHCO_3$, and water again until neutral, dried, then evaporated to dryness in vacuo. After crystallization from methanol, 2.21 g of the 4′R-methyl-2′-bromotrans-enone was obtained, m.p. 109.5°–111° C, in 82.3% yield.

EXAMPLE 11

To a solution pre-cooled to −15° to −20° C of 300 mg of NaBH$_4$ in 35 ml of methanol was added a solution of 4.3 g of 5β-(2′-bromo-3′-oxo-4′R-methyl-oct-1′-trans-1′-enyl)-2α,4α-dihydroxycyclopentane-1α-acetic acid-γ-lactone-4-p-phenyl-benzoate in 30 ml of methanol. The reduction was complete after 30 minutes, the excess reagent was destroyed by addition of 3.3 ml of 15% aqueous acetic acid. After concentration under vacuum to 5–8 ml, the mixture was partitioned between water and dichloroethane. The organic phase was separated, washed until neutral, dried and after concentration to 7–8 ml the residue was chromatographed on 800 g of silica gel and eluted with methylene chloride:ethyl ether (95:5). The first fraction obtained contained 2.72 g of 5β-(2′-bromo-3′S-hydroxy-4′R-methyl-oct-1′-trans-1′-enyl)-2α,4α-dihydroxycyclopentane-1α-acetic acid-γ-lactone-4-p-phenylbenzoate [α]$_D$ = 59° (CHCl$_3$), and the second was 1.24 g of the corresponding 3′-epimer [after crystallization from isopropyl ether, m.p. 87°–88°, [α]$_D$ = −82° (CHCl$_3$)].

EXAMPLE 12

Starting with the corresponding 2′-bromo-3′-oxo-derivatives, as in Examples 1–11, by reduction with zinc borohydride in ether, as described in Example 6, or by reduction with sodium borohydride, as described in Example 11, after chromatographic separation on silica gel (using ratios of mixture of alcohols to silica gel from 1/100 to 1/250, and either methylene chloride or methylene chloride:ethyl ether mixtures for elution), the following alcohols were prepared: dl-5β-(2′-bromo-3′S-hydroxy-oct-1′-trans-1′-enyl)-2α,4α-dihydroxycyclopentane-1α-acetic acid-γ-lactone-4-acetate; dl-5β-(2′-bromo-3′R-hydroxy-oct-1′-trans-1′-enyl)-2α,4α-dihydroxycyclopentane-1α-acetic acid-γ-lactone-4-acetate; the following 2α,4α-dihydroxy-cyclopentane-1α-acetic acid-γ-lactone-4-p-phenylbenzoates:

5β-(2′-bromo-3′S-hydroxy-oct-1′-trans-1′-enyl) and its 3′R epimer;

5β-(2′-bromo-3′S-hydroxy-4′S-methyl-oct-1′-trans-1′-enyl) [α]$_D$ = −74.6° (CHCl$_3$) and its 3′R epimer [α]$_D$ = −91° C (CHCl$_3$); 5β-(2′-bromo-3′S-hydroxy-4′R-methyl-oct-1′-trans-1′-enyl) and its 3′-R epimer;

5β-(2′-bromo-3′S-hydroxy-non-1′-trans-1′-enyl), m.p. 72°–75°, [α]$_D$ = −100° (CHCl$_3$) and its 3′R epimer.

5β-(2′-bromo-3′S-hydroxy-4′S-methyl-non-1′-trans-1′-enyl) [α]$_D$ = −78° (CHCl$_3$) and its 3′R epimer [α]$_D$ = −96° (CHCl$_3$);

5β-(2′-bromo-3′S-hydroxy-4′R-methyl-non-1′-trans-1′-enyl) [α]$_D$ = −64° (CHCl$_3$) and its 3′R epimer [α]$_D$ = −88° (CHCl$_3$);

5β-(2′-bromo-3′S-hydroxy-dec-1′-trans-1′-enyl) [α]$_D$ = −98° (CHCl$_3$) and its 3′R epimer;

and the following 4-p-phenylbenzoates of 2β,4α-dihydroxycyclopentane-1β-acetic acid-γ-lactone:

5α-(2′-bromo-3′S-hydroxy-oct-1′-trans-1′-enyl) and its 3′R epimer;

5α-(2′-bromo-3′S-hydroxy-4′S-methyl-oct-1′-trans-1′-enyl) and its 3′R-epimer;

5α-(2′-bromo-3′S-hydroxy-non-1′-trans-1′-enyl), [α]$_D$ = − 166° (CHCl$_3$) and its 3′R epimer, [α]$_D$ = −167° (CHCl$_3$);

5α-(2′-bromo-3′S-hydroxy-4′S-methyl-non-1′-trans-1′-enyl) and its 3′R epimer;

5α-(2′-bromo-3′-hydroxy-dec-1′-trans-1′-enyl) and its 3′R epimer.

EXAMPLE 13

Anhydrous K$_2$CO$_3$ (0.5 g) was added to a stirred solution of 1.66 g of 5β-(2′-bromo-3′S-hydroxy-4′S-methyl-oct-1′-trans-1′-enyl)-2α,4α-dihydroxy-cyclopentane-1α-acetic acid-γ-lactone-p-phenylbenzoate in dry methanol (50 ml).

After 2 hours, the mixture was neutralized with a saturated solution of NaH$_2$PO$_4$, filtered and the filtrate evaporated to dryness. The residue was taken up in ethyl acetate, which was washed until neutral, dried and the solvent removed under vacuum.

The residue was chromatographed on 10 g of silica gel, eluted with cyclohexane:ethyl acetate 80:20, to give 1.1 g of 5β-(2′-bromo-3′S-hydroxy-4′S-methyl-oct-1′-trans-1′-enyl)-2α,4α-dihydroxy-cyclopentane-1α-acetic acid-γ-lactone.

An aliquot recrystallized from ethyl ether showed a m.p. of 71°–73° C, [α]$_D$ = −13.7°, [α]$_{365°}$ = −40° (CHCl$_3$). A solution of this compound (1.1 g) in dry benzene (25 ml) was treated with 1,4-DIOX-2-ene (0.45 g) and with a solution of p-toluensulfonic acid (6 mg) in benzene, for 3 hours at room temperature, and then washed with 3% aqueous K$_2$CO$_3$ and with water until neutral. After removal of the solvent in vacuum, 1.52 g of 5β-(2′-bromo-3′S-hydroxy-4′S-methyl-oct-1′-trans-1′-enyl)-2α,4α-dihydroxy-cyclopentane-1α-acetic acid-γ-lactone-2,4-bis-DIOX-ether, [α]$_D$ = −20.3° (CHCl$_3$) were obtained.

EXAMPLE 14

Starting with the 4-esters of the alcohols described in Example 12 and using the procedure described in Examples 6 and 13, saponification in dry methanol with 1.2 equivalent of K$_2$CO$_3$ affords the crude free alcohols which are reacted with a vinyl ether selected from 2,3-dihydropyran and 1,4-DIOX-2-ene (2.5–3 moles/mole of alcohol) in benzene, in the presence of a catalytic amount of p-toluene sulfonic acid (1 × 10$^{-2}$ moles/mole of alcohol) to give the corresponding 3′,4-bis-THP-ethers and 3′,4-bis-DIOX-ethers of the following 2α,4α-dihydroxycyclopentane-1α-acetic acid-γ-lactones:

dl-5β-(2′-bromo-3′S-hydroxy-oct-1′-trans-1′-enyl) and its 3′R epimer;

5β-(2′-bromo-3′S-hydroxy-oct-1′-trans-1′-enyl) and its 3′S epimer;

5β-(2′-bromo-3′S-hydroxy-4′S-methyl-oct-1′-trans-1′-enyl), [α]$_D$ = −21.3° (CHCl$_3$) and its 3′R epimer;

5β-(2′-bromo-3′S-hydroxy-4′R-methyl-oct-1′-trans-1′-enyl) and its 3′R epimer;

5β-(2′-bromo-3′S-hydroxy-4′(R,S)-methyl-oct-1′-trans-1′-enyl) and its 3′R epimer;

5β-(2′-bromo-3′S-hydroxy-non-1′-trans-1′-enyl) and its 3′R epimer;

5β-(2′-bromo-3′S-hydroxy-4′S-methyl-non-1′-trans-1′-enyl) and its 3′R epimer;

5β-(2′-bromo-3′S-hydroxy-4′R-methyl-non-1′-trans-1′-enyl) and its 3′R epimer;

5β-(2′-bromo-3′S-hydroxy-dec-1′-trans-1′-enyl) and its 3′R epimer;

5β-(2'-bromo-3'S-hydroxy-4'(R,S)-methyl-dec-1'-trans-1'-enyl) and its 15R epimer;
and also the following 2β, 4α-dihydroxy-cyclopentane-1β-acetic acid-γ-lactones:
5α-(2'-bromo-3'S-hydroxy-oct-1'-trans-1'-enyl) and its 3'R epimer;
5α-(2'-bromo-3'S-hydroxy-4'S-methyl-oct-1'-trans-1'-enyl) and its 3'R epimer;
5α-(2'-bromo-3'S-hydroxy-non-1'-trans-1'-enyl) and its 3'R epimer;
5α-(2'-bromo-3'S-hydroxy-4'S-methyl-non-1'-trans-1'-enyl) and its 3'R epimer;
5α-(2'-bromo-3'S-hydroxy-dec-1'-trans-1'-enyl) and its 3'R epimer.

All of these compounds were characterized by the absence of the OH bands in the IR spectra and by the intense absorptions between 1250–950 cm$^{-1}$, due to the ether linkages.

EXAMPLE 15

With humidity exclusion, under a nitrogen atmosphere, a solution of 5β-(2'-bromo-3'S-hydroxy-non-1'-trans-1'-enyl)-2α,4α-dihydroxy-cyclopentane-1αacetic acid-γ-lactone-3',4-bis-THP-ether (0.57 g) in dry toluene (10 ml) was cooled at −70° C and then 0.5 DIBA solution in toluene (4.6 ml) was added, dropwise, over a period of 20 minutes, maintaining the temperature of the reaction mixture below −60° C. After an additional stirring at −70° C for 20' 5 ml of 2M isopropanol in toluene was added.

The mixture was warmed for 15 minutes at 0° C, then 1 ml of water, 3 g of sodium sulfate and 3 g of Kieselgur were added. After stirring for 4 hours at room temperature, it was filtered and evaporated to dryness, giving 0.56 g of 5β-(2'-bromo-3'S-hydroxy-non-1'-trans-1'-enyl)-2α,4α-dihydroxy-cyclopentane-1α-ethanal-γ-lactol-3',4-bis-THP-ether, showing an HO band in the IR spectra.

EXAMPLE 16

Under nitrogen atmosphere, with humidity exclusion, a mixture of toluene (8 ml) and a 70% solution of sodium bis-(2-methoxyethoxy)-alluminium hydride in benzene (2.22 ml) was added dropwise to a solution of 5β-(2'-bromo-3'S-hydroxy-4'S-methyl-oct-1'-trans-1'-enyl)-2α,4α-dihydroxy-cyclopentane-1α-acetic acid-γ-lactone-3',4-bis-DIOX-ether (2.56 g) in anhydrous toluene (60 ml), cooled to −60° to −65° C.

After stirring for 3 hours the excess reagent was destroyed by careful addition of a 5% solution of acetone in toluene.

After 10 minutes, the mixture was warmed to 0°–2° C, and treated with 3 ml of a saturated solution of NaH$_2$PO$_4$. The crystalline precipitate was filtered out and the filtrate evaporated to dryness in vacuo to give 2.5 g of 5β-(2'-bromo-3'S-hydroxy-4'S-methyl-oct-1'-trans-1'-enyl)-2α, 4α-dihydroxy-cyclopentane-1α-ethanal-γ-lactol-3',4-bis-DIOX-ether, with an OH band in the IR spectra.

EXAMPLE 17

A solution of 0.54 g of 5β-(2'-bromo-3'S-hydroxy-oct-1'-trans-1'-enyl)-2α,4α-dihydroxy-cyclopentane-1α-acetic acid-γ-lactone-4-p-phenylbenzoate in 18 ml of toluene, cooled to −70° C, was treated, as outlined in Example 15, with 8 ml of a solution of 0.5 ml of DIBA in toluene. After standing for 30 minutes at −70° C, it is then treated with a 2M solution of isopropanol in toluene to destroy the excess reagent.

It is warmed to 0° C, then 1.5 ml of water, 5 g of sodium sulfate and 5 g of Kieselgur are added. After filtration, the filtrate is evaporated to dryness and chromatographed on 6 g of silica gel, with cyclohexane-ethylacetate (60:40) as eluent, to give 0.36 g of 5β-(2'-bromo-3'S-hydroxy-4'S-methyl-oct-1'-trans-1'-enyl)-2α,4α-dihydroxy-cyclopentane-1α-ethanal-γ-lactol.

The same product was obtained starting from the 3',4-bis-DIOX-ether (270 mg), which was dissolved in 10 ml of acetone and refluxed with 6 ml of a solution of 0.2N oxalic acid in water, for 90 minutes. The acetone was removed in vacuo and the residue extracted with ethyl acetate. The combined organic phases were washed until neutral and evaporated to dryness to give 0.17 g of 5β-(2'-bromo-3'S-hydroxy-4'S-methyl-oct-1'-trans-1'-enyl)-2α,4α-dihydroxy-cyclopentane-1α-ethanal-γ-lactol. (Intense OH band and disappearance of intense absorptions between 1150 and 950 cm$^{-1}$).

EXAMPLE 18

Starting from the γ-lactone alcohols and their acetalic ethers (3',4-bis-THP-ethers and bis-DIOX-ethers), as in Examples 14, or with their 4-esters, as in Example 12, using the procedures described in Examples 15, 16 and 17, we prepared as free alcohols and as their corresponding 3',4-bis-THP-ethers and 3',4-bis-DIOX-ethers the following 2α,4α-dihydroxy-cyclopentane-1α-ethanol-γ-lattols:
 dl-5β-(2'-bromo-3'S-hydroxy-oct-1'-trans-1'-enyl) and its 3'R-hydroxy epimer;
 5β-(2'-bromo-3'S-hydroxy-oct-1'-trans-1'-enyl) and its 3'R epimer;
 5β-(2'-bromo-3'S-hydroxy-4'S-methyl-oct-1'-trans-1'-enyl), [α]$_D$ = −29° (CHCl$_3$) (as THP-ether), and its 3'R epimer;
 5β-(2'-bromo-3'S-hydroxy-4'R-methyl-oct-1'-trans-1'-enyl) and its 3'R epimer;
 5β-(2'-bromo-3'S-hydroxy-4'(R,S)-methyl-oct-1'-trans-1'-enyl) and its 3'R epimer;
 5β-(2'-bromo-3'S-hydroxy-non-1'-trans-1'-enyl) and its 3'R epimer;
 5β-(2'-bromo-3'S-hydroxy-4'S-methyl-non-1'-trans-1'-enyl) and its 3'R epimer;
 5β-(2'-bromo-3'S-hydroxy-4'R-methyl-non-1'-trans-1'-enyl and its 3'R epimer;
 5β-(2'-bromo-3'S-hydroxy-dec-1'-trans-1'-enyl) and its 3'R epimer;
 5β-(2'-bromo-3'S-hydroxy-4'(R,S)-methyl-dec-1'-trans-1'-enyl) and its 15R epimer;
and the following 2β,4α-dihydroxy-cyclopentane-1β-ethanal-γ-lactols:
 5α-(2'-bromo-3'S-hydroxy-oct-1'-trans-1'-enyl) and its 3'R epimer;
 5α-(2'-bromo-3'S-hydroxy-4'S-methyl-oct-1'-trans-1'-enyl) and its 3'R epimer;
 5α-(2'-bromo-3'S-hydroxy-non-1'-trans-1'-enyl) and its 3'R epimer;
 5α-(2'-bromo-3'S-hydroxy-4'S-methyl-non-1'-trans-1'-enyl) and its 3'R epimer;
 5α-(2'-bromo-3'S-hydroxy-dec-1'-trans-1'-enyl) and its 3'R epimer.

EXAMPLE 19

Working in dry conditions, under a nitrogen atmosphere, a suspension of 232 mg of 80% sodium hydride (dispersion in mineral oil) in 6 ml of DMSO was warmed to 58°-65° until no more hydrogen was evolved. It was cooled to 4°-8° C then 1.7 g of triphenyl-(4-carboxybutyl)-phosphonium bromide was added all at once and stirred until completely dissolved, with formation of a dark red solution of the ylide. Next, a solution of 0.3 g of 5β-(2'-bromo-3'R-hydroxy-non-1'-trans-1'-enyl)-2α,4α-dihydroxycyclopentane-1α-ethanal-γ-lactol-3',4-bis-THP-ether in 4 ml of DMSO was added. The mixture was stirred for 45 minutes with the temperature maintained at approximately 15° C, then diluted with 12 ml of water and the alkaline mixture was extracted 12 times with 3 ml of ethyl ether. The combined ether extracts were back-washed 4 times with 2 ml of 1N NaOH and discarded. The alkaline aqueous fractions were combined, acidified to pH 4.5 with 2N $H_2SO_4$ and extracted with ethyl ether-pentane 1:1.

These organic extracts were combined, washed until neutral, dried on $Na_2SO_4$ and evaporated to dryness, to give 288 mg of 5c-9α,11α,15R-trihydroxy-20ω-homo-prost-5-en-13-ynoic acid-11,15-bis-THP-ether, $[\alpha]_D = +18.4°$ (EtOH). This product was dissolved in 15 ml of acetone and after the solution had been cooled to $-20°$ C, 0.9 ml of Jones' reagent was added. After standing for 40 minutes at $-15°$ to $-10°$ C, it was diluted with 3 volumes of benzene. This was washed repeatedly with saturated ammonium sulfate solution until neutral, dried on $MgSO_4$ and evaporated to dryness. The residue contained 270 mg of 5c-9-oxo-11α,15R-dihydroxy-20ω-homo-prost-5-en-13-ynoic acid-11,15-bis-THP-ether which was dissolved in 12 ml of acetone and treated with 15 ml of 0.2N oxalic acid, at 40° C, for 6 hours.

The acetone was removed under vacuum (on a water bath at a temperature no more than 40° C), and the aqueous phase was extracted repeatedly with ethyl ether.

The combined organic phases were washed until neutral, dried and the solvent removed in vacuo. The residue was chromatographed on 2 g of silicic acid and eluted with methylene chloride and $CH_2Cl_2$-ethyl acetate 80:20, to give 92 mg of pure 5c-9-oxo-11α,15R-dihydroxy-20ω-homoprost-5-en-13-ynoic acid, $[\alpha]_D = -17°$ (1% ethanol) (15-epi-13,14-dehydro-20ω-$PGE_2$).

EXAMPLE 20

Working in dry conditions under nitrogen atmosphere, a suspension of 0.39 g of NaH (80% dispersion in mineral oil) in 12 ml of dry dimethylsulfoxide was warmed to 60°-62° C until no more hydrogen was evolved. The solution was then cooled to 5°-10° C and 2.83 g of triphenyl-(4-carboxybutyl)-phosphonium bromide was added all at once. The mixture was maintained at 13°-14° C and stirred until all the reagent has dissolved. A strongly colored red solution of the ylide was formed. At that time, a solution of 0.375 g of 5β-(2'-bromo-3'S-hydroxy-dec-1'-trans-1'-enyl)-2α,4α-dihydroxycyclopentane-1α-ethanal-γ-lactol in 3 ml of DMSO was added and the mixture stirred for 6 hours.

The mixture was cooled to about 15°-16° C and diluted with 15 ml of water, then extracted 15 times with 3 ml of ethyl ether to remove the triphenylphosphoxide formed in the reaction. The combined organic extracts were backwashed with 0.5N NaOH (3 × 4 ml) and discarded.

All the aqueous phases were combined, acidified to pH 5 and extracted 5 times with 10 ml of ethyl ether and 2 times with 10 ml of ethyl ether-ethyl acetate (70:30). The combined organic phases were washed with saturated $(NH_4)_2SO_4$ solution, dried and the solvent removed by evaporation, yielding 0.56 g of a crude product which was chromatographed on 4 g of silicic acid gel and eluted with methylene chloride and mixtures of increasing amounts of ethyl acetate in methylene chloride. From the fraction eluted with $CH_2Cl_2$:ethyl acetate 60:40, 0.25 g of pure 5c-9α,11α,15S-trihydroxy-20ω-dihomo-prost-5-en-13-ynoic acid was obtained, $[\alpha]_D = +26°$ (EtOH), (13,14-dehydro-20ω-dihomo-$PGF_{2\alpha}$).

EXAMPLE 21

Under a nitrogen atmosphere a suspension of 1.49 g of NaH (80% dispersion in mineral oil) in 40 ml of DMSO was warmed to 60°-65° C, with stirring and with exclusion of humidity for 3 hours, until no more hydrogen was evolved. It was cooled to 5°-8° C and 10.93 g of triphenyl-(4-carboxybutyl)-phosphonium bromide was added all at once. The material was kept at 15° C and stirred until all the reagent was dissolved, giving a DMSO solution of the ylide $(C_6H_5)_3P-CH_{(-)}-(CH_2)_3COO^{(-)}$.

To the solution of the ylide was added a solution of 1.75 g of 5β-(2'-bromo-3'S-hydroxy-4'S-methyl-oct-1'-trans-1'-enyl)-2α,4α-dihydroxy-cyclopentane-1α-ethanal-γ-lactol-3',4-bis-DIOX-ether $[\alpha]_D = -28°$ ($CHCl_3$) in 5 ml of DMSO. This was left to stand at room temperature for 4 hours, then diluted with 45 ml of water and extracted with ethyl ether to remove the triphenylphoshoxide. The ether extracts were combined, backwashed with 0.5N NaOH and discarded.

The aqueous alkaline phases were combined, acidified to pH 4.5 with 2N sulfuric acid and extracted with ethyl ether-pentane 1:1. The organic extracts were combined, washed with saturated $(NH_4)_2SO_4$ until neutral, dried and the solvent evaporated off. The residue weighed 1.82 g and consisted of crude 5c-9α,11α,15S-trihydroxy-16S-methyl-prost-5-en-13-ynoic acid-11α,15S-bis-dioxanyl-ether, $[\alpha]_D = +7°$ ($CHCl_3$).

Using the procedures described for Examples 19, 20 and 21, and starting from the γ-lactol-3'S,4-bis-THP-ethers and the γ-lactol-3'S,4-bis-DIOX-ethers, of which Example 18 is one, the 11α,15S-bis-THP-ethers and 11α,15S-bis-DIOX-ethers of the following prostanoic acids were obtained:

dl-5c-9α,11α,15S-trihydroxy-prost-5-en-13-ynoic acid;

5c-9α,11α,15S-trihydroxy-prost-5-en-13-ynoic acid, $[\alpha]_D = -18°$ ($CHCl_3$);

5c-9α,11α,15S-trihydroxy-16S-methyl-prost-5-en-13-ynoic acid;

5c-9α,11α,15S-trihydroxy-16R-methyl-prost-5-en-13-ynoic acid, $[\alpha]_D = +9°$ ($CHCl_3$);

5c-9α,11α,15S-trihydroxy-20ω-homo-prost-5-en-13-ynoic acid, $[\alpha]_D = +7°$ ($CHCl_3$);

5c-9α,11α,15S-trihydroxy-20ω-homo-16S-methyl-prost-5-en-13-ynoic acid, $[\alpha]_D = +12°$ ($CHCl_3$);

5c-9α,11α,15S-trihydroxy-20ω-homo-16R-prost-5-en-13-ynoic acid, $[\alpha]_D = +11°$ ($CHCl_3$);

5c-9α,11α,15S-trihydroxy-20ω-dihomo-prost-5-en-13-ynoic acid;

5c-9β,11α,15S-trihydroxy-8,12-diiso-prost-5-en-13-ynoic acid;

5c-9β,11α,15S-trihydroxy-16S-methyl-8,12-diiso-prost-5-en-13-ynoic acid;

5c-9β,11α,15S-trihydroxy-20ω-homo-8,12-diiso-prost-5-en-13-ynoic acid, $[\alpha]_D = -12°$ ($CHCl_3$);

5c-9β,11α,15S-trihydroxy-16S-methyl-20ω-homo-8,12-diiso-prost-5-en-13-ynoic acid;

5c-9β,11α,15S-trihydroxy-20ω-dihomo-8,12-diiso-prost-5-en-13-ynoic acid.

EXAMPLE 22

Under nitrogen, with humidity exclusion, a solution of 0.54 g (1 × 10⁻³ moles) of 5α-(2'-bromo-3'R-hydroxy-dec-1'-trans-1'-enyl)-2β,4α-dihydroxy-cyclopentane-1α-ethanal-γ-lactol-3'R,4-bis-THP-ether in 3 ml of DMSO was added to a DMSO solution of the carbanion of the ylide $(C_6H_5)_3P\text{-}CH_{(-)}\text{-}(CH_2)_3\text{-}CO^{(-)}$ obtained by reacting 120 mg of NaH (4 × 10⁻³ moles) as an 80% dispersion in mineral oil with 890 mg of triphenyl-(4-carboxybutyl)-phosphonium bromide (2 × 10⁻³ moles), as described in examples 19 to 21. After 1 hour and 45 minutes, the mixture was diluted with 10 ml of water and extracted with ether to remove the triphenylphosphoxide.

The ether extracts were back-washed with 0.5N NaOH and discarded. The aqueous alkaline phases were combined, acidified to pH 4.7 and extracted with ethyl ether-pentane 1:1. The combined organic phases were washed until neutral and evaporated to dryness to give 0.49 g of 5c-9β,11α,15R-trihydroxy-20ω-dihomo-8,12-diiso-prost-5-en-13-ynoic acid-11,15-bis-THP-ether, $[\alpha]_D = -14°$ (EtOH).

Using the methodology outlined in Examples 19–22, and starting from the γ-lactol-3'R,4-bis-THP-ethers and the γ-lactol-3'R,4-bis-DIOX-ethers, as shown in Example 18, the 11,15R-bis-THP-ethers and the 11,15R-bis-DIOX-ethers of the following prostanoic acids were obtained:

dl-5c-9α,11α,15R-trihydroxy-prost-5-en-13-ynoic acid;
5c-9α,11α,15R-trihydroxy-prost-5-en-13-ynoic acid;
5c-9α,11α,15R-trihydroxy-16S-methyl-prost-5-en-13-ynoic acid;
5c-9α,11α,15R-trihydroxy-16R-methyl-prost-5-en-13-ynoic acid;
5c-9α,11α,15R-trihydroxy-20ω-homo-prost-5-en-13-ynoic acid;
5c-9α,11α,15R-trihydroxy-16S-methyl-20ω-homo-prost-5-en-13-ynoic acid;
5c-9α,11α,15R-trihydroxy-16R-methyl-20ω-homo-prost-5-en-13-ynoic acid;
5c-9α,11α,15R-trihydroxy-20ω-dihomo-prost-5-en-13-ynoic acid;
5c-9β,11α,15R-trihydroxy-8,12-diiso-prost-5-en-13-ynoic acid;
5c-9β,11α,15R-trihydroxy-16S-methyl-8,12-diiso-prost-5-en-13-ynoic acid;
5c-9β,11α,15R-trihydroxy-20ω-homo-8,12-diiso-prost-5-en-13-ynoic acid;
5c-9β,11α,15R-trihydroxy-16S-methyl-20ω-homo-8,12-diiso-prost-5-en-13-ynoic acid;
5c-9β,11α,15R-trihydroxy-20ω-dihomo-8,12-diiso-prost-5-en-13-ynoic acid.

EXAMPLE 23

To a DMSO solution of the ylide prepared from 120 g of NaH (80% dispersion in mineral oil) and 890 mg of triphenyl-(4-carboxybutyl)-phosphonium bromide, prepared as described in Example 20, under nitrogen and protected from humidity was added a solution of 0.18 g of 5β-(2'-bromo-3'R-hydroxy-4'S-methyl-oct-1'-trans-1'-enyl)-2α,4α-dihydroxycyclopentane-1α-ethanal-γ-lactol in 1.5 ml of DMSO. This was stirred for 5 hours, then diluted with 5 ml of water. The alkaline aqueous phase was repeatedly extracted with ether to remove the triphenylphosphoxide.

The organic extracts were back-washed with 0.5 N NaOH and discarded. The combined aqueous phases were acidified to pH 4.8 and extracted with ethyl ether. The ether extracts from this extraction were combined, washed until neutral and evaporated to dryness. The residue was chromatographed on silicic acid gel and eluted with dichloromethane-ethyl acetate to give 0.12 g of 5c-9α,11α,15R-trihydroxy-16S-methyl-prost-5-en-13-ynoic acid, $[\alpha]_D = +28°$ (EtOH) (13,14-dehydro-16S-methyl-15-epi-PGF$_{2\alpha}$).

EXAMPLE 24

A solution of 0.25 g of 5c-9α,11α,15S-trihydroxy-16S-methyl-prost-5-en-13-ynoic acid-11,15-bis-DIOX-ether in 10 ml of acetone and 8 ml of 0.2N oxalic acid was refluxed for one hour. The acetone was removed under vacuum and the residue partitioned between water and ethyl ether. The ether layer was washed until neutral, dried and evaporated to dryness.

The residue was chromatographed on 1.2 g of silicic acid gel, eluted with CH$_2$Cl$_2$-ethyl acetate 60:40, to give 132 mg of 5c-9α,11α,15S-trihydroxy-16S-methyl-prost-5-en-13-ynoic acid, $[\alpha]_D = +30°$ (EtOH) (13,14-dehydro-16S-methyl-PGF$_{2\alpha}$).

EXAMPLE 25

Using the procedures described in Examples 20 and 23 and starting with the free 3'S,4-dihydroxy-γ-lactols, as in Example 18, by reaction of the ylide in DMSO, obtained with triphenyl-(4-carboxy-butyl)-phosphonium bromide, the following compounds were prepared:

13,14-dehydro-PGF$_{2\alpha}$, $[\alpha]_D = +28°$ (EtOH) and its racemate, m.p. 81°–82° C;
13,14-dehydro-16S-methyl-PGF$_{2\alpha}$, $[\alpha]_D = +30°$ (EtOH);
13,14-dehydro-16R-methyl-PGF$_{2\alpha}$, $[\alpha]_D = +28.9°$ (EtOH);
13,14-dehydro-16R-methyl-PGF$_{2\alpha}$, $[\alpha]_D = +29°$ (EtOH);
13,14-dehydro-20ω-homo-PGF$_{2\alpha}$, $[\alpha]_D = +30.7°$ (EtOH);
13,14-dehydro-16S-methyl-20ω-homo-PGF$_{2\alpha}$, $[\alpha]_D = +31°$ (EtOH);
13,14-dehydro-16R-methyl-20ω-homo-PGF$_{2\alpha}$, $[\alpha]_D = +30.2°$ (EtOH);
13,14-dehydro-15S-methyl-20ω-homo-PGF$_{2\alpha}$, $[\alpha]_D = +26°$ (EtOH);
15-epi-13,14-dehydro-PGF$_{2\alpha}$, $[\alpha]_D = +31.6°$ (EtOH) and its racemate (oil);
15-epi-13,14-dehydro-16S-methyl-PGF$_{2\alpha}$, $[\alpha]_D = +30.4°$ (EtOH);
15-epi-13,14-dehydro-16(S,R)-methyl-PGF$_{2\alpha}$, $[\alpha]_D = +29°$;
15-epi-13,14-dehydro-20ω-homo-PGF$_{2\alpha}$, $[\alpha]_D = +33.8°$ (EtOH);
15-epi-13,14-dehydro-16S-methyl-20ω-homo-PGF$_{2\alpha}$, $[\alpha]_D = +26°$ (EtOH);
15-epi-13,14-dehydro-16R-methyl-20ω-homo-PGF$_{2\alpha}$, $[\alpha]_D = +31°$ (EtOH);
15-epi-13,14-dehydro-20ω-dihomo-PGF$_{2\alpha}$, $[\alpha]_D = +32°$ (EtOH);
13,14-dehydro-8,12-diiso-PGF$_{2\beta}$, $[\alpha]_D = -2°$ (EtOH);
13,14-dehydro-16S-methyl-8,12-diiso-PGF$_{2\beta}$;
13,14-dehydro-20ω-homo-8,12-diiso-PGF$_{2\beta}$;

13,14-dehydro-16S-methyl-20ω-homo-8,12-diiso-PGF$_{2\beta}$;
13,14-dehydro-20ω-dihomo-8,12-diiso-PGF$_{2\beta}$, $[\alpha]_D = -6°$ (CHCl$_3$);
15-epi-13,14-dehydro-8,12-diiso-PGF$_{2\beta}$;
15-epi-13,14-dehydro-16S-methyl-8,12diiso-PGF$_{2\beta}$;
15-epi-13,14-dehydro-20ω-homo-8,12-diiso-PGF$_{2\beta}$;
15-epi-13,14-dehydro-16S-methyl-20ω-homo-8,12-diiso-PGF$_{2\beta}$;
15-epi-13,14-dehydro-20ω-dihomo-8,12-diiso-PGF$_{2\beta}$.

These compounds may be also obtained starting from the acetalic (THP and DIOX)-ethers of the Example 21 and following the procedure described in Example 24.

EXAMPLE 26

To a solution of 0.54 g of 5c-9α,11α,15S-trihydroxy-16S-methyl-prost-5-en-13-ynoic acid-11,15-bis-DIOX-ether in 1.5 ml of hexamethylenephosphoramide was added 0.1 ml of 50% NaOH (w/v) and the mixture was stirred for one hour. Then 140 mg of propyl bromide was added, and the mixture stirred overnight. Then 8 ml of water were added and the mixture was acidified to pH 4.5 with 2N H$_2$SO$_4$ and extracted with ethyl ether. The ether extracts were washed until neutral and evaporated to dryness to give 0.57 g of 5c-9α, 11α, 15S-trihydroxy-16S-methyl-prost-5-en-13-ynoic acid-11,15-bis-DIOX-ether propyl ester.

Using this same procedure, starting with the 11,15-bis-acetalic ethers (11,15-bis-THP-ethers and 11,15-bis-DIOX-ethers), as in Examples 21 and 22, and substituting for the propyl bromide another alkyl-halide (for instance, methyl iodide, ethyl iodide, butyl bromide, octyl bromide, decyl bromide), the methyl, ethyl, propyl, butyl, octyl or decyl esters of the prost-5-en-13-ynoic acids were prepared.

These compounds were all characterized by IR spectra showing the characteristic ester band at 1720 cm$^{-1}$.

EXAMPLE 27

0.72 g of 5c-9α,11α,15S-trihydroxy-16S-methyl-prost-5-en-13-ynoic acid-propyl ester-11,15-bis-DIOX-ether was dissolved in 14 ml of acetone, cooled to −18° C and then had added to it over a 4 minutes period 1.4 ml of Jones' reagent.

This was allowed to warm up to −12° to −10° C and left at that temperature for 20 minutes. It was then diluted with 45 ml of benzene, then washed once with 10 ml and 8 times with 3 ml of a saturated solution of (NH$_4$)$_2$SO$_4$ until it tested neutral, dried and the solvent evaporated off. In this way 0.67 g of 5c-9-oxo-11α,15S-dihydroxy-16S-methyl-prost-5-en-13-ynoic acid-propyl ester-11,15-bis-DIOX-ether, which was dissolved in 30 ml of acetone. To this solution, 40 ml of 0.1N oxalic acid were added and the mixture left to stand for 6 hours at 36°–38° C. The acetone was distilled off under vacuum, at about 40° C, and the aqueous phase was extracted with ether, which was again evaporated to dryness. The residue was chromatographed on silica gel (10 g) with cyclohexane-ethyl acetate 75:25 as eluent, to give 0.43 g of 16S-methyl 5c-9-oxo-11α,15S-dihydroxy-prost-5-en-13-ynoic acid-propyl ester (13,14-dehydro-16S-methyl-PGE$_2$-propyl ester), $[\alpha]_D = -14.2°$ (EtOH).

EXAMPLE 28

A solution of 1.4 g of 16S-methyl-13,14-dehydro-PGF$_{2\alpha}$-11,15-bis-dioxanylether in 28 ml of acetone was treated at −18° C with 2.8 ml of Jones' reagent, added over a 5 minutes period.

The mixture was maintained at −10° to −12° C for 20 minutes then diluted with 80 ml of benzene, washed with a saturated solution of ammonium sulfate until neutral and dried, yielding 1.35 g of the 16S-methyl-13,14-dehydro-PGE$_2$-11,15-bis-DIOX-ether.

A solution of this compound in 60 ml of acetone was allowed to react for 8 hours at 40°–42° C with a 0.2N solution of citric acid.

The acetone was evaporated and the aqueous mixture was extracted several times with ethyl ether. The combined organic extracts were dried and the solvent removed in vacuo. The residue was chromatographed in acid silica gel and eluted with CH$_2$Cl$_2$-ethyl acetate 65:35 to give 0.7 g of 16S-methyl-13,14-dehydro-PGE$_2$, $[\alpha]_D = -16.3°$ C (EtOH).

EXAMPLE 29

Starting with one of the 11,15-bis-acetalic ethers (11,15-bis-THP-ethers or 11,15-bis-DIOX-ethers) of 13,14-dehydro-PGF$_2$ prepared as described in Examples 21 or 23, or from one of their esters as in Example 26, by oxidation with Jones' reagent in acetone, and using the procedures outlined in Examples 27 and 28, the 11,15-bis-acetalic ethers of 13,14-dehydro-PGE$_2$ were prepared, both as free acids and as esters which were then deacetalated by the procedures in Examples 27 and 28. In this way, the following compounds were prepared, as free acids:

13,14-dehydro-PGE$_2$, $[\alpha]_D = -15.1°$ (EtOH) and its racemate (oil);
13,14-dehydro-16S-methyl-PGE$_2$, $[\alpha]_D = -16.3°$ (EtOH);
13,14-dehydro-16R-methyl-PGE$_2$, $[\alpha]_D = -19.4°$ (EtOH), $[\alpha]_{365°} = -165°$ (CHCl$_3$);
13,14-dehydro-20ω-homo-PGE$_2$, $[\alpha]_D = -14.2°$ (EtOH), m.p. 42°;
13,14-dehydro-16S-methyl-20ω-homo-PGE$_2$, $[\alpha]_D = -16.6°$ (CHCl$_3$);
13,14-dehydro-16R-methyl-20ω-homo-PGE$_2$, $[\alpha]_D = -18.8°$ (CHCl$_3$);
13,14-dehydro-20ω-dihomo-PGE$_2$, $[\alpha]_D = -15°$ (EtOH);
13,14-dehydro-8,12-diiso-PGE$_2$, $[\alpha]_D = +11°$ (CHCl$_3$);
13,14-dehydro-16S-methyl-8,12-diiso-PGE$_2$, $[\alpha]_D = +13°$ (CHCl$_3$);
13,14-dehydro-20ω-homo-8,12-diiso-PGE$_2$, $[\alpha]_D = +9.9°$ (CHCl$_3$); $[\alpha]_{365°} = +143°$ (CHCl$_3$);
13,14-dehydro-16S-methyl-20ω-homo-8,12-diiso-PGE$_2$;
15-epi-13,14-dehydro-PGE$_2$, $[\alpha]_D = -13.3°$ (CHCl$_3$), and its racemate (oil);
15-epi-13,14-dehydro-16S-methyl-PGE$_2$, $[\alpha]_D = -19°$ (CHCl$_3$);
15-epi-13,14-dehydro-16R-methyl-PGE$_2$, $[\alpha]_D = +15.3°$ (CHCl$_3$); $[\alpha]_{365°} = -161°$ (CHCl$_3$);
15-epi-13,14-dehydro-20ω-homo-PGE$_2$, $[\alpha]_D = -17°$ (CHCl$_3$);
15-epi-13,14-dehydro-16S-methyl-20ω-homo-PGE$_2$;
15-epi-13,14-dehydro-16R-methyl-20ω-homo-PGE$_2$, $[\alpha]_D = -16°$ (CHCl$_3$);
15-epi-13,14-dehydro-20ω-dihomo-PGE$_2$, $[\alpha]_D = -14°$ (CHCl$_3$);
15-epi-13,14-dehydro-8,12-diiso-PGE$_2$;
15-epi-13,14-dehydro-16S-methyl-8,12-diiso-PGE$_2$;
15-epi-13,14-dehydro-20ω-homo-8,12-diiso-PGE$_2$, $[\alpha]_D = -11.5°$ (CHCl$_3$), $[\alpha]_{365°} = +94°$ (CHCl$_3$);

15-epi-13,14-dehydro-16S-methyl-20ω-homo-8,12-diiso-PGE$_2$;

15-epi-13,14-dehydro-20ω-dihomo-8,12-diiso-PGE$_2$, and their esters (methyl, ethyl, propyl, n-octyl, n-decyl) as well as their 11,15-bis-acetalic derivatives.

EXAMPLE 30

A solution of 0.29 g of 5c-9-oxo-11α,15S-dihydroxy-16S-methyl-prost-5-en-13-ynoic acid-n-propylester-11,15-bis-DIOX-ether, $[\alpha]_D = -9.7°$ (THF), in 20 ml of acetone and 17 ml of 0.25N aqueous oxalic acid was refluxed for 6 hours and after removal of the acetone in vacuo, the aqueous phase was extracted several times with ether-CH$_2$Cl$_2$ 5:1. The combined organic phase was washed with saturated ammonium sulfate until neutral, dehydrated and evaporated to dryness. The residue was purified by preparative thin-layer chromatography (eluent cyclohexane-ether) to give 5c-9-oxo-15S-hydroxy-16S-methyl-prosta-5,10-dien-13-ynoic acid-n-propyl ester (0.13 g), 13,14-dehydro-16S-methyl-PGA$_2$.

EXAMPLE 31

In procedure of Example 30, when the prostenoic derivative was replaced by 5c-9-oxo-11α,15S-dihydro-20ω-homo-prost-5-en-13-ynoic acid-11,15-bis-THP-ether (0.21 g), the product obtained after silica gel column chromatography with cylohexane-ether (70:30) was 5c-9-oxo-15S-hydroxy-20ω-homo-prosta-5,10-dien-13-ynoic acid (20ω-homo-13,14-dehydro-PGA$_2$).

EXAMPLE 32

Using the methods outlined in Examples 30 and 31, the 13,14-dehydro-9-oxo-prostadienoic acid-11,15-bis-ethers of Example 29, either as free acids or as esters, had their ether groups removed at reflux temperatures with acetone-0.2N aqueous oxalic acid, yielding esters (methyl, ethyl, propyl, n-butyl, n-octyl and n-decyl) or free acids of the following optically active compounds:

13,14-dehydro-PGA$_2$ and its 15R-epimer;
13,14-dehydro-16S-methyl-PGA$_2$ and its 15R-epimer;
13,14-dehydro-16R-methyl-PGA$_2$ and its 15R-epimer;
13,14-dehydro-16(R,S)-methyl-PGA$_2$ and its 15R-epimer;
13,14-dehydro-20ω-homo-PGA$_2$ and its 15R-epimer;
13,14-dehydro-16S-methyl-20ω-homo-PGA$_2$ and its 15R-epimer;
13,14-dehydro-16R-methyl-20ω-homo-PGA$_2$ and its 15R-epimer;
13,14-dehydro-20ω-dihomo-PGA$_2$ and its 15R-epimer;
13,14-dehydro-16(R,S)-dimethyl-20ω-dihomo-PGA$_2$ and its 15R-epimer;
13,14-dehydro-8,12-diiso-PGA$_2$ and its 15R-epimer;
13,14-dehydro-16S-methyl-8,12-diiso-PGA$_2$ and its 15R-epimer;
13,14-dehydro-20ω-homo-8,12-diiso-PGA$_2$ and its 15R-epimer;
13,14-dehydro-16S-methyl-20ω-homo-8,12-diiso-PGA$_2$ and its 15R-epimer;
13,14-dehydro-20ω-dihomo-8,12-diiso-PGA$_2$ and its 15R-epimer.

EXAMPLE 33

A solution of dimethyl-(2-oxo-heptyl)-phosphonate (3.32 g) in benzene (10 ml) was added to a stirred suspension of 80% NaH (mineral oil dispersion) (0.45 g) in dry benzene (40 ml). After additional stirring for 1 hour, the reaction mixture in the dark was treated with N-iodo-succinimide (3.4 g). After 45 minutes, a solution of 5β-formyl-(2α,4α-dihydroxycyclopentane-1α-acetic acid-γ-lactone-4-p-phenylbenzoate was added to a solution of the carbanion of dimethyl-(1-iodo-2-oxo-heptyl)-phosphonate, cooled at 2°–4° C. The stirring was lasted for 45 minutes, then the reaction mixture was diluted with water, the organic layer was separated, washed with 5% NaH$_2$PO$_4$, 5% Na$_2$S$_2$O$_3$, water until neutral, dried and evaporated to dryness in vacuum.

The crude enone was chromatographed on SiO$_2$ to afford 2.4 g of 5β-(2'-iodo-3'-oxo-oct-1'-trans-1'-enyl)-2α, 4α-dihydroxy-cyclopentane-1α-acetic acid-γ-lactone-4-p-phenylbenzoate.

Following reduction with Zn(BH$_4$)$_2$ in ether afforded 5β-(2'-iodo-3'S-hydroxy-oct-1'-trans-1'-enyl)-2α,4α-dihydroxy-cyclopentane-1α-acetic acid-γ-lactone-4-p-phenylbenzoate and its 3'R-isomer.

Selective saponification with K$_2$CO$_3$ in dry methanol followed by acetalization with 2,3-dihydropyran gave 5β-(2'-iodo-3'S-hydroxy-oct-1'-trans-1'-enyl)-2α,4α-dihydroxy-cyclopentane-1α-acetic acid-γ-lactone-3',4-bis-THP-ether which was treated with 1.2 molar equivalent of DIBA in toluene at −70° C.

By reaction of the resulting 2'-iodo-γ-lactol with 2.5 molar equivalent of the disodium salt of the triphenyl-(4-carboxy-butyl)-phosphonium bromide in DMSO 13,14-dehydro-PGE$_{2\alpha}$-11,15-bis-THP-ether was obtained.

We claim:

1. A compound of the formula:

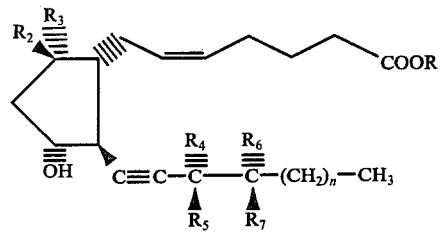

wherein:
R is hydrogen, a C$_1$–C$_{12}$ alkyl group or a cation of a pharmaceutically acceptable base;
R$_2$ and R$_3$ taken together form an oxo group;
one of R$_4$ and R$_5$ is hydrogen and the other is a hydroxy group;
R$_6$ is a 16(S) C$_1$–C$_4$ alkyl group and R$_7$ is hydrogen; and
n is an integer of 3 to 6.

2. The compound according to claim 1 wherein R$_4$ is hydroxy and R$_5$ is hydrogen.

3. A compound of the formula:

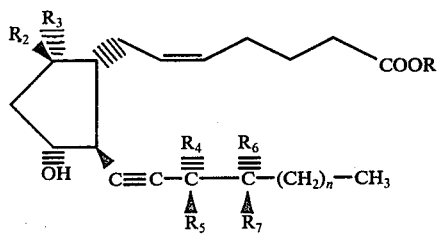

wherein:
R is hydrogen, a C$_1$–C$_{12}$ alkyl group or a cation of a pharmaceutically acceptable base;

$R_2$ and $R_3$ taken together form an oxo group;

one of $R_4$ and $R_5$ is hydrogen and the other is a hydroxy group;

$R_6$ is hydrogen and $R_7$ is a 16(R) $C_1$–$C_4$ alkyl group; and $n$ is an integer from 3 to 6.

4. The compound according to claim 3 wherein $R_4$ is hydroxy and $R_5$ is hydrogen.

5. The compound 16S-methyl-5c-9-oxo-11α,15S-dihydroxy-prost-5-en-13-ynoic acid, its salt or $C_1$–$C_{12}$ alkyl ester thereof.

6. The $C_1$–$C_{12}$ alkyl ester of the compound of claim 5.

7. The compound: 16S-methyl-5c-9-oxo-11α,15S-dihydroxy-prost-5-en-13-ynoic acid propyl ester.

8. The compound: 16R-methyl-5c-9-oxo-11α,15S-dihydroxy-prost-5-en-13 ynoic acid, its salt or $C_1$–$C_{12}$ alkyl ester thereof.

9. The $C_1$–$C_{12}$ alkyl ester of the compound of claim 8.

10. The compound 16S-methyl-5c-9-oxo-11α,15S-dihydroxy-20ω-homo-prost-5-en-13-ynoic acid, its salt or $C_1$–$C_{12}$ alkyl ester thereof.

11. The $C_1$–$C_{12}$ alkyl ester of the compound of claim 10.

12. The compound 16R-methyl-5c-9-oxo-11α,15S-dihydroxy-20ω-homo-prost-5-en-13-ynoic acid, its salt or $C_1$–$C_{12}$ alkyl ester thereof,

13. The $C_1$–$C_{12}$ alkyl ester of the compound of claim 12.

* * * * *

UNITED STATES PATENT OFFICE
CERTIFICATE OF CORRECTION

Patent No. 4,041,064          Dated August 9, 1977

Inventor(s) Carmelo Gandolfi; Gianfederico Doria; Renato Pellegata; Maria M. Usardi It is certified that error appears in the above-identified patent and that said Letters Patent are hereby corrected as shown below:

Column 1, lines 30 and 31 should read: "14-chloro-$\Delta^{13(14)}$-ethylene prostaglandin analogues";

Column 13, line 55, between the two formulae insert --and their racemates, wherein $R_2$ is hydrogen and $R_3$ is hydroxy or $R_2$ and $R_3$ together form an oxo group,--;

line 66, insert "wherein $R_2$ is hydroxy and $R_3$ is hydrogen or $R_2$ and $R_3$ together form an oxo group,";

Column 14, line 22, delete "either" insert --ethyl--;
       line 66 should read, "wherein B may be $-C\equiv C-$ or $-CH=C\overset{X'}{\underset{}{|}}$ Column 15, line 11, delete X and insert --X'--;
       line 25, $R_2$ should be linked to the pentatomic ring by bond ▲ ;

Column 16, line 40, delete "X" insert --Z--;
       lines 54 and 55 rewrite as follows: --The reaction between the lactol of formula (II) wherein B is $-C\equiv C-$ or--;

Column 17, line 39, change "ame" to --same--;

UNITED STATES PATENT OFFICE
CERTIFICATE OF CORRECTION

Patent No. 4,041,064              Dated August 9, 1977

Inventor(s)   Gandolfi, et al

It is certified that error appears in the above-identified patent and that said Letters Patent are hereby corrected as shown below:

Column 18, lines 1 to 10, the upper part of the formula
should be redrawn as follows:

line 42, the meaning of B is "-C≡C-";

Column 20, lines 1-10, the upper part of the formula is not
complete, insert --COOR-- at the end of the chain;
line 30, delete "of rate" insert --of rats--;
line 36, correct the spelling of "stabilize";
line 41, correct the spelling of "ileum";

Column 25, line 42, after "pyridine" correct the spelling of
"trifluoroacetate";

Column 26, delete line 16;

UNITED STATES PATENT OFFICE
CERTIFICATE OF CORRECTION

Patent No. 4,041,064     Dated August 9, 1977

Inventor(s) Gandolfi, et al

It is certified that error appears in the above-identified patent and that said Letters Patent are hereby corrected as shown below:

Column 27, line 24, delete "338°" insert -- -338° --;

Column 29, line 24, delete "59°" insert -- -59° --;

Column 31, line 25, after "0.5" and before "DIBA" insert --M--

Signed and Sealed this

Eighteenth Day of April 1978

[SEAL]

Attest:

RUTH C. MASON
*Attesting Officer*

LUTRELLE F. PARKER
*Acting Commissioner of Patents and Trademarks*